(12) United States Patent
MacDonald et al.

(10) Patent No.: US 10,439,148 B2
(45) Date of Patent: Oct. 8, 2019

(54) COMPOUND, LIGHT EMITTING MATERIAL, AND ORGANIC LIGHT EMITTING DEVICE

(71) Applicant: NIPPON STEEL CHEMICAL & MATERIAL CO., LTD., Tokyo (JP)

(72) Inventors: James MacDonald, Bentleigh East (AU); Melissa Skidmore, Parkdale (AU); Kazunori Ueno, Glen Waverley (AU); Hiroshi Miyazaki, Kitakyushu (JP); Chihaya Adachi, Fukuoka (JP)

(73) Assignee: NIPPON STEEL CHEMICAL & MATERIAL CO., LTD., Tokyo (JP)

( * ) Notice: Subject to any disclaimer, the term of this patent is extended or adjusted under 35 U.S.C. 154(b) by 495 days.

(21) Appl. No.: 14/909,182

(22) PCT Filed: Jul. 29, 2014

(86) PCT No.: PCT/JP2014/069891
§ 371 (c)(1),
(2) Date: Feb. 1, 2016

(87) PCT Pub. No.: WO2015/016200
PCT Pub. Date: Feb. 5, 2015

(65) Prior Publication Data
US 2016/0172600 A1 Jun. 16, 2016

(30) Foreign Application Priority Data
Aug. 1, 2013 (JP) ................... 2013-160826

(51) Int. Cl.
*C07D 401/10* (2006.01)
*H01L 51/00* (2006.01)
(Continued)

(52) U.S. Cl.
CPC ........ *H01L 51/0067* (2013.01); *C07D 401/10* (2013.01); *C07D 401/14* (2013.01);
(Continued)

(58) Field of Classification Search
CPC ............. H01L 51/0067; H01L 51/0052; H01L 51/0071; H01L 51/0068; H01L 51/0094;
(Continued)

(56) References Cited

U.S. PATENT DOCUMENTS 8,476,397 B2 7/2013 Kobayashi
9,761,811 B2 * 9/2017 Suda ..................... C07F 7/0816
(Continued)

FOREIGN PATENT DOCUMENTS

CN 102131843 A 7/2011
JP 06312982 A 8/1994
(Continued)

OTHER PUBLICATIONS

Uoyama et al., Highly efficient organic light-emitting diodes from delayed fluorescence, Dec. 13, 2012, Nature, vol. 492, 234-240.*
(Continued)

*Primary Examiner* — Eli D. Strah
(74) *Attorney, Agent, or Firm* — Browdy and Neimark, PLLC

(57) ABSTRACT

A compound represented by the general formula (1) is useful as a light emitting material. In the general formula (1), $Ar^1$ to $Ar^3$ represent an aryl group, provided that $Ar^2$ and $Ar^3$ are the same as each other, and at least one of $Ar^1$ to $Ar^3$ represents an aryl group substituted with a group represented by the general formula (2). In the general formula (2), $R^1$ to $R^8$ represent a hydrogen atom or a substituent; Z represents O, S, $R^9$—N, $(R^{10})(R^{11})C$, or $(R^{12})(R^{13})Si$; and $R^9$ to $R^{13}$ each independently represent a hydrogen atom or a substituent.

(Continued)

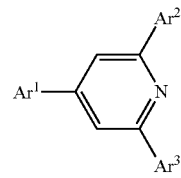

(1)

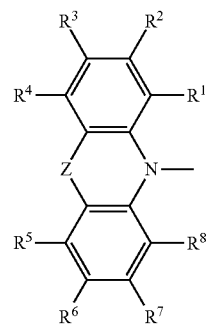

(2)

6 Claims, 10 Drawing Sheets

(51) Int. Cl.
| | |
|---|---|
| C07D 409/14 | (2006.01) |
| C09K 11/06 | (2006.01) |
| C07D 401/14 | (2006.01) |
| C07D 413/14 | (2006.01) |
| C07D 413/10 | (2006.01) |
| C07D 417/14 | (2006.01) |
| C09B 67/22 | (2006.01) |
| C09B 67/46 | (2006.01) |
| C07F 7/08 | (2006.01) |
| C09B 15/00 | (2006.01) |
| C09B 17/00 | (2006.01) |
| C09B 17/02 | (2006.01) |
| C09B 19/00 | (2006.01) |
| C09B 21/00 | (2006.01) |
| C09B 57/00 | (2006.01) |
| C09B 69/00 | (2006.01) |
| G02F 1/1335 | (2006.01) |
| G02F 1/137 | (2006.01) |
| H01L 51/50 | (2006.01) |

(52) U.S. Cl.
CPC ......... *C07D 409/14* (2013.01); *C07D 413/10* (2013.01); *C07D 413/14* (2013.01); *C07D 417/14* (2013.01); *C07F 7/0816* (2013.01); *C09B 15/00* (2013.01); *C09B 17/00* (2013.01); *C09B 17/02* (2013.01); *C09B 19/00* (2013.01); *C09B 21/00* (2013.01); *C09B 57/00* (2013.01); *C09B 67/009* (2013.01); *C09B 67/0041* (2013.01); *C09B 69/008* (2013.01); *C09K 11/06* (2013.01); *H01L 51/0052* (2013.01); *H01L 51/0068* (2013.01); *H01L 51/0071* (2013.01); *H01L 51/0072* (2013.01); *H01L 51/0094* (2013.01); *B32B 2457/206* (2013.01); *C09K 2211/104* (2013.01); *C09K 2211/1007* (2013.01); *C09K 2211/1011* (2013.01); *C09K 2211/1029* (2013.01); *C09K 2211/1033* (2013.01); *C09K 2211/1037* (2013.01); *C09K 2211/1044* (2013.01); *C09K 2211/1092* (2013.01); *G02F 1/13762* (2013.01); *G02F 2001/133614* (2013.01); *H01L 51/5012* (2013.01)

(58) Field of Classification Search
CPC . H01L 51/0072; H01L 51/5012; C09B 17/00; C09B 17/02; C09B 21/00; C09B 15/00; C09B 69/008; C09B 57/00; C09B 19/00; C09B 67/0041; C09B 67/009; C07F 7/0816; C07D 401/10; C07D 401/14; C07D 413/10; C07D 413/14; C07D 417/14; C07D 409/14; C09K 11/06; C09K 2211/1007; C09K 2211/1011; C09K 2211/1092; C09K 2211/1044; C09K 2211/1029; C09K 2211/1033; C09K 2211/1037; C09K 2211/104; G02F 1/13762; G02F 2001/133614; B32B 2457/206

See application file for complete search history.

(56) References Cited

U.S. PATENT DOCUMENTS

| | | | |
|---|---|---|---|
| 2010/0171417 A1* | 7/2010 | Kitamura | C07D 401/10 313/504 |
| 2012/0248968 A1 | 10/2012 | Ogiwara et al. | |
| 2013/0020558 A1 | 1/2013 | Ogiwara | |
| 2014/0061548 A1 | 3/2014 | Montenegro et al. | |
| 2014/0070146 A1 | 3/2014 | Parham et al. | |

FOREIGN PATENT DOCUMENTS

| | | |
|---|---|---|
| JP | 2000186066 A | 7/2000 |
| JP | 2009170815 A | 7/2009 |
| JP | 201031259 A | 2/2010 |
| JP | 2010180204 A | 7/2010 |
| JP | 2011210749 A | 10/2011 |
| KR | 20120095832 A | 8/2012 |
| KR | 1020130115160 A | 10/2013 |
| KR | 20140076521 A | 6/2014 |
| KR | 20140079315 A | 6/2014 |
| WO | 2012067415 A2 | 5/2012 |
| WO | 2012108879 A1 | 8/2012 |
| WO | 2012149999 A1 | 11/2012 |
| WO | 2013100603 A1 | 7/2013 |

OTHER PUBLICATIONS

International Search Opinion, dated Feb. 4, 2015 in corresponding application No. PCT/JP2014069891.
International Preliminary Report on Patentability, dated Feb. 4, 2015 in corresponding application No. PCT/JP2014069891.
Office Action for corresponding Taiwanese Patent Application No. 103126495, dated Jan. 15, 2018, with English translation.
European search report for European application No. 14831835.5 dated Mar. 2, 2017.
Office Action for corresponding Chinese Patent Application No. 201480043477.6, dated May 5, 2017, with English translation.

* cited by examiner

COMPOUND, LIGHT EMITTING MATERIAL, AND ORGANIC LIGHT EMITTING DEVICE

TECHNICAL FIELD

The present invention relates to a compound that is useful as a light emitting material, and an organic light emitting device using the same.

BACKGROUND ART

An organic light emitting device, such as an organic electroluminescent device (organic EL device), has been actively studied for enhancing the light emission efficiency thereof. In particular, various studies for enhancing the light emitting efficiency have been made by newly developing and combining an electron transporting material, a hole transporting material, a light emitting material and the like constituting an organic electroluminescent device. There are studies relating to an organic electroluminescent device utilizing a compound containing a nitrogen-containing heteroaromatic ring and a carbazole structure, and some proposals have been made hitherto.

For example, Patent Document 1 proposes that a compound containing a nitrogen-containing heteroaromatic ring and a carbazole structure represented by the following general formula is used as a host material in a light emitting layer present between a pair of electrodes constituting an organic electroluminescent device. In the following general formula, Cz group represents a substituted or unsubstituted arylcarbazolyl group or a carbazolylalkylene group. In the following general formula, A represents a group represented by $(M)_p$-$(L)_q$-$(M')_r$, in which M and M' each independently represent a substituted or unsubstituted nitrogen-containing heteroaromatic ring having from 2 to 40 carbon atoms, and L represents a single bond, a substituted or unsubstituted aryl or arylene group having from 6 to 30 carbon atoms, a substituted or unsubstituted cycloalkylene group having from 5 to 30 carbon atoms, or a substituted or unsubstituted heteroaromatic ring having from 2 to 30 carbon atoms. p is from 0 to 2, q is 1 or 2, r is from 0 to 2, p+r is an integer of 1 or more, and n and m each are from 1 to 3. Patent Document 1 describes, as one example, that a compound containing a pyridine ring and a carbazolyl structure is used as a host material of a light emitting layer. However, Patent Document 1 does not describe the light emission characteristics of the compound represented by the general formula, and does not describe a compound having an analogous structure other than a carbazole structure.

$(Cz\text{-})_n A$ $(Cz)(\text{-}A)_m$

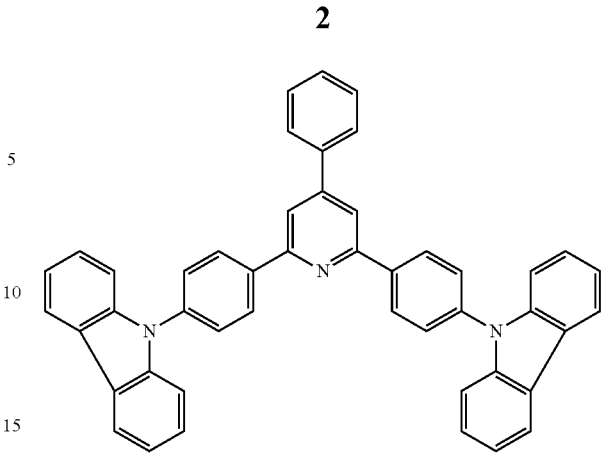

CITATION LIST

Patent Literature

Patent Document 1: WO 2012/108879

SUMMARY OF INVENTION

Technical Problem

As described in the foregoing, Patent Document 1 describes that a compound containing a nitrogen-containing heteroaromatic ring and a carbazole structure is useful as a host material of a light emitting layer of an organic electroluminescent device. However, there has been no study on as to whether or not the compound described in Patent Document 1 is capable of functioning as a light emitting material. A light emitting material is different in demanded properties and functions from a host material, and therefore the usefulness of the compound represented by the general formula of Patent Document 1 as a light emitting material is unknown. Furthermore, Patent Document 1 describes a compound containing a pyridine ring and a carbazole structure, but does not describe a compound having an analogous skeleton other than a pyridine ring and a carbazole structure, and the usefulness as a light emitting material cannot be expected therefrom.

In consideration of the related art problems, the present inventors have made investigations on an object of synthesizing compounds containing in the molecules thereof both a pyridine ring, and a phenoxazine structure, a phenothiazine structure, a phenazine structure, a 9,10-dihydroacridine structure, or a heterocyclic structure obtained by replacing the carbon atom at the 9-position of the dihydroacridine structure by a silicon atom, and evaluating the usefulness as a light emitting material. Furthermore, the inventors have made earnest investigations on an object of providing the general formula of the compound that is useful as a light emitting material, and generalizing the structure of an organic light emitting device having a high light emission efficiency.

Solution to Problem

As a result of earnest investigations for achieving the objects, the inventors have succeeded at the synthesis of compounds containing both a pyridine ring, and a phenoxazine structure, a phenothiazine structure, a phenazine structure, a 9,10-dihydroacridine structure, or a heterocyclic structure obtained by replacing the carbon atom at the 9-position of the dihydroacridine structure by a silicon atom, and have firstly clarified that the compounds are useful as a light emitting material. Furthermore, the inventors have found that the compounds include ones that are useful as a delayed fluorescent material, and have clarified that an organic light emitting device having a high light emission efficiency can be provided inexpensively. Based on the knowledge, the inventors have provided the invention shown below as a measure for solving the problem.

(1) A compound represented by the following general formula (1):

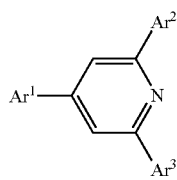

General Formula (1)

wherein in the general formula (1), $Ar^1$ to $Ar^3$ each independently represent a substituted or unsubstituted aryl group, provided that $Ar^2$ and $Ar^3$ are the same as each other, and at least one of $Ar^1$ to $Ar^3$ represents an aryl group substituted with a group represented by the following general formula (2):

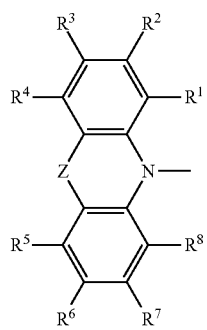

General Formula (2)

wherein in the general formula (2), $R^1$ to $R^8$ each independently represent a hydrogen atom or a substituent; Z represents O, S, $R^9$—N, $(R^{10})(R^{11})$ C, or $(R^{12})(R^{13})$Si; and $R^9$ to $R^{13}$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(2) The compound according to the item (1), wherein when $Ar^1$ to $Ar^3$ each represent a substituted aryl group, the substituent substituted on the aryl group is selected from the group consisting of a substituent represented by the general formula (2), an alkyl group having from 1 to 6 carbon atoms, an aryl group having from 6 to 14 carbon atoms, and an aralkyl group having from 7 to 15 carbon atoms.

(3) The compound according to the item (1), wherein in the general formula (1), at least one of $Ar^1$ to $Ar^3$ represents an aryl group substituted with a group represented by the following general formula (3):

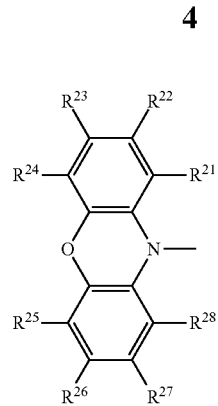

General Formula (3)

wherein in the general formula (3), $R^{21}$ to $R^{28}$ each independently represent a hydrogen atom or a substituent, provided that $R^{21}$ and $R^{22}$, $R^{22}$ and $R^{23}$, $R^{23}$ and $R^{24}$, $R^{25}$ and $R^{26}$, $R^{26}$ and $R^{27}$, and $R^{27}$ and $R^{28}$ each may be bonded to each other to form a cyclic structure.

(4) The compound according to the item (1), wherein in the general formula (1), at least one of $Ar^1$ to $Ar^3$ represents an aryl group substituted with a group represented by the following general formula (4):

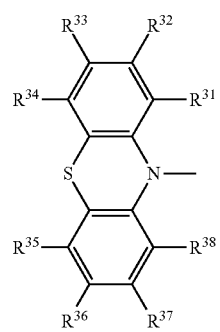

General Formula (4)

wherein in the general formula (4), $R^{31}$ to $R^{38}$ each independently represent a hydrogen atom or a substituent, provided that $R^{31}$ and $R^{32}$, $R^{32}$ and $R^{33}$, $R^{33}$ and $R^{34}$, $R^{35}$ and $R^{36}$, $R^{36}$ and $R^{37}$, and $R^{37}$ and $R^{38}$ each may be bonded to each other to form a cyclic structure.

(5) The compound according to the item (1), wherein in the general formula (1), at least one of $Ar^1$ to $Ar^3$ represents an aryl group substituted with a group represented by the following general formula (5):

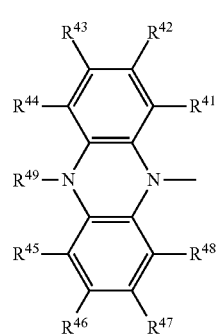

General Formula (5)

wherein in the general formula (5), $R^{41}$ to $R^{49}$ each independently represent a hydrogen atom or a substituent, provided that $R^{41}$ and $R^{42}$, $R^{42}$ and $R^{43}$, $R^{43}$ and $R^{44}$, $R^{45}$ and $R^{46}$, $R^{46}$ and $R^{47}$, and $R^{47}$ and $R^{48}$ each may be bonded to each other to form a cyclic structure.

(6) The compound according to the item (1), wherein in the general formula (1), at least one of $Ar^1$ to $Ar^3$ represents an aryl group substituted with a group represented by the following general formula (6):

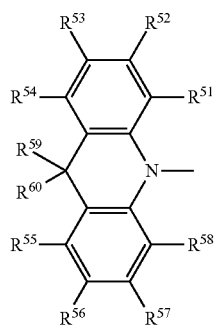

General Formula (6)

wherein in the general formula (6), $R^{51}$ to $R^{60}$ each independently represent a hydrogen atom or a substituent, provided that $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, and $R^{59}$ and $R^{60}$ each may be bonded to each other to form a cyclic structure.

(7) The compound according to the item (1), wherein in the general formula (1), at least one of $Ar^1$ to $Ar^3$ represents an aryl group substituted with a group represented by the following general formula (7):

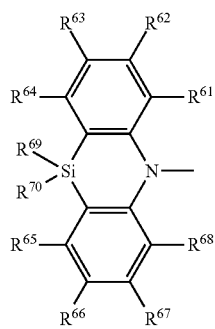

General Formula (7)

wherein in the general formula (7), $R^{61}$ to $R^{70}$ each independently represent a hydrogen atom or a substituent, provided that $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, and $R^{69}$ and $R^{70}$ each may be bonded to each other to form a cyclic structure.

(8) The compound according to the item (1), wherein the compound is represented by the following general formula (8):

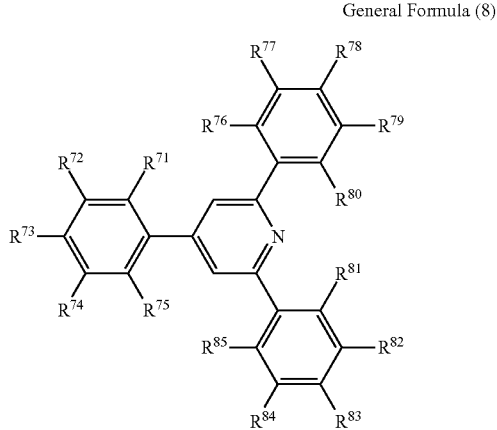

General Formula (8)

wherein in the general formula (8), at least one of $R^{71}$ to $R^{85}$ represents a group represented by the following general formula (2); and the other thereof each independently represent a hydrogen atom or a substituent other than a substituent represented by the general formula (2), provided that $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$, $R^{79}$ and $R^{80}$, $R^{81}$ and $R^{82}$, $R^{82}$ and $R^{83}$, $R^{83}$ and $R^{84}$, and $R^{84}$ and $R^{85}$ each may be bonded to each other to form a cyclic structure:

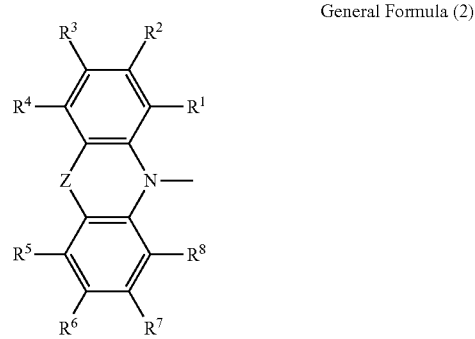

General Formula (2)

wherein in the general formula (2), $R^1$ to $R^8$ each independently represent a hydrogen atom or a substituent; Z represents O, S, $R^9$—N, $(R^{10})$ $(R^{11})$ C, or $(R^{12})$ $(R^{13})$Si; and $R^9$ to $R^{13}$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(9) The compound according to the item (8), wherein in the general formula (8), at least one of $R^{71}$ to $R^{85}$ represents a group represented by the following general formula (3):

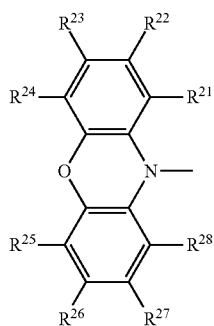

General Formula (3)

wherein in the general formula (3), $R^{21}$ to $R^{28}$ each independently represent a hydrogen atom or a substituent, provided that $R^{21}$ and $R^{22}$, $R^{22}$ and $R^{23}$, $R^{23}$ and $R^{24}$, $R^{25}$ and $R^{26}$, $R^{26}$ and $R^{27}$, and $R^{27}$ and $R^{28}$ each may be bonded to each other to form a cyclic structure.

(10) The compound according to the item (8), wherein in the general formula (8), at least one of $R^{71}$ to $R^{85}$ represents a group represented by the following general formula (4):

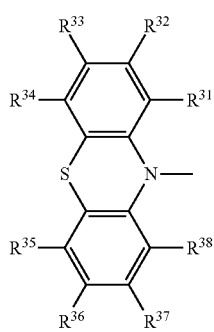

General Formula (4)

wherein in the general formula (4), $R^{31}$ to $R^{38}$ each independently represent a hydrogen atom or a substituent, provided that $R^{31}$ and $R^{32}$, $R^{32}$ and $R^{33}$, $R^{33}$ and $R^{34}$, $R^{35}$ and $R^{36}$, $R^{36}$ and $R^{37}$, and $R^{37}$ and $R^{38}$ each may be bonded to each other to form a cyclic structure.

(11) The compound according to the item (8), wherein in the general formula (8), at least one of $R^{71}$ to $R^{85}$ represents a group represented by the following general formula (5):

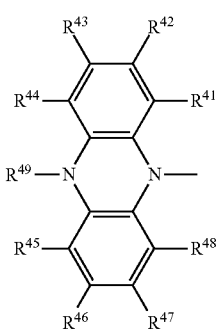

General Formula (5)

wherein in the general formula (5), $R^{41}$ to $R^{49}$ each independently represent a hydrogen atom or a substituent, provided that $R^{41}$ and $R^{42}$, $R^{42}$ and $R^{43}$, $R^{43}$ and $R^{44}$, $R^{45}$ and $R^{46}$, $R^{46}$ and $R^{47}$, and $R^{47}$ and $R^{48}$ each may be bonded to each other to form a cyclic structure.

(12) The compound according to the item (8), wherein in the general formula (8), at least one of $R^{71}$ to $R^{85}$ represents a group represented by the following general formula (6):

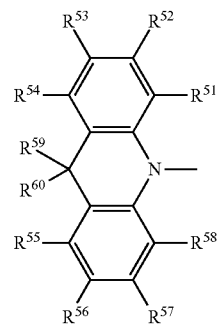

General Formula (6)

wherein in the general formula (6), $R^{51}$ to $R^{60}$ each independently represent a hydrogen atom or a substituent, provided that $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, and $R^{59}$ and $R^{60}$ each may be bonded to each other to form a cyclic structure.

(13) The compound according to the item (8), wherein in the general formula (8), at least one of $R^{71}$ to $R^{85}$ represents a group represented by the following general formula (7):

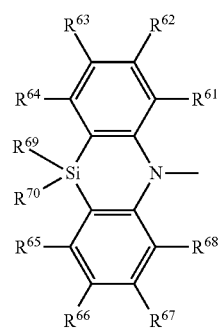

General Formula (7)

wherein in the general formula (7), $R^{61}$ to $R^{70}$ each independently represent a hydrogen atom or a substituent, provided that $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, and $R^{69}$ and $R^{70}$ each may be bonded to each other to form a cyclic structure.

(14) A light emitting material containing the compound according to any one of the items (1) to (13).

(15) A delayed fluorescent emitter having a structure represented by the following general formula (1):

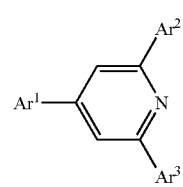

General Formula (1)

wherein in the general formula (1), $Ar^1$ to $Ar^3$ each independently represent a substituted or unsubstituted aryl group, provided that $Ar^2$ and $Ar^3$ are the same as each other, and at least one of $Ar^1$ to $Ar^3$ represents an aryl group substituted with a group represented by the following general formula (2):

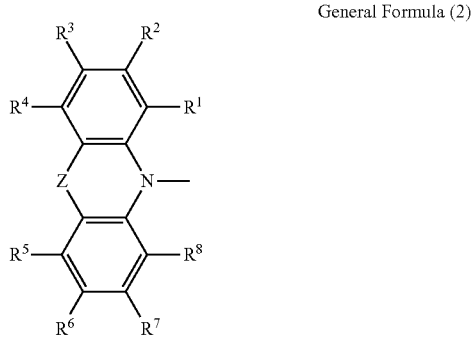

General Formula (2)

wherein in the general formula (2), $R^1$ to $R^8$ each independently represent a hydrogen atom or a substituent; Z represents O, S, $R^9$—N, $(R^{10})(R^{11})$ C, or $(R^{12})(R^{13})$Si; and $R^9$ to $R^{13}$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

(16) An organic light emitting device containing a substrate having thereon a light emitting layer containing the light emitting material according to the item (14).

(17) The organic light emitting device according to the item (16), wherein the organic light emitting device emits delayed fluorescent light.

(18) The organic light emitting device according to the item (16) or (17), wherein the organic light emitting device is an organic electroluminescent device.

Advantageous Effects of Invention

The compound of the invention is useful as a light emitting material. The compound of the invention includes one that emits delayed fluorescent light. The organic light emitting device using the compound of the invention as a light emitting material is capable of achieving a high light emission efficiency.

DESCRIPTION OF EMBODIMENTS

Figure 1:
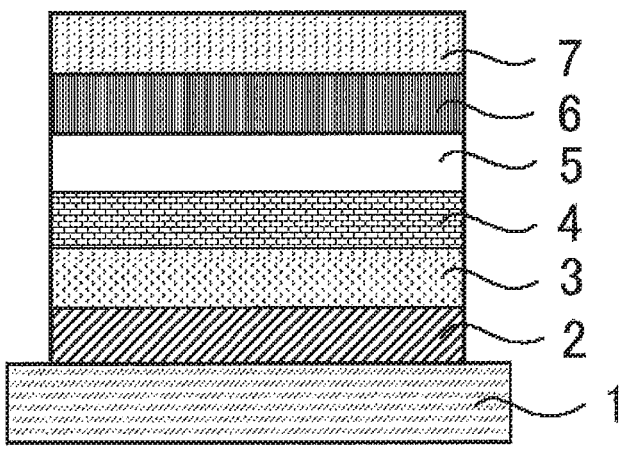
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the compound used in the invention is not particularly limited in isotope species, and for example, all the hydrogen atoms in the molecule may be $^1H$, and all or a part of them may be $^2H$ (deuterium (D)).

Compound represented by General Formula (1) The compound of the invention has the structure represented by the following general formula (1):

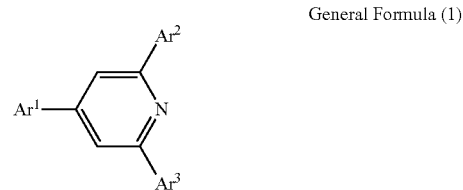

General Formula (1)

wherein in the general formula (1), $Ar^1$ to $Ar^3$ each independently represent a substituted or unsubstituted aryl group, provided that $Ar^2$ and $Ar^3$ are the same as each other, and at least one of $Ar^1$ to $Ar^3$ represents an aryl group substituted with a group represented by the following general formula (2):

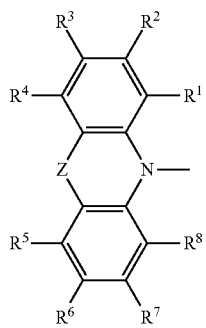

General Formula (2)

wherein in the general formula (2), $R^1$ to $R^8$ each independently represent a hydrogen atom or a substituent; Z represents O, S, $R^9$—N, $(R^{10})(R^{11})$ C, or $(R^{12})(R^{13})$ Si; and $R^9$ to $R^{13}$ each independently represent a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure.

The aromatic ring constituting the aryl group represented by $Ar^1$ to $Ar^3$ in the general formula (1) may be a monocyclic ring or a condensed ring, and specific examples thereof include a benzene ring, a naphthalene ring, an anthracene ring, and a phenanthrene ring. The aryl group preferably has from 6 to 40 carbon atoms, more preferably from 6 to 20 carbon atoms, and further preferably from 6 to 14 carbon atoms. At least one of $Ar^1$ to $Ar^3$ represents an aryl group substituted with a group represented by the general formula (2). Two of $Ar^1$ to $Ar^3$ each may be an aryl group substituted with a group represented by the general formula (2), and three of them each may be an aryl group substituted with a group represented by the general formula (2). One aryl group may be substituted with two or more groups each represented by the general formula (2). For the descriptions and the preferred ranges of the substituent that is capable of being substituted on the aryl group represented by $Ar^1$ to $Ar^3$, reference may be made to the descriptions and the preferred ranges of the substituent represented by $R^1$ to $R^8$ described later. However, the aromatic rings constituting the aryl groups represented by $Ar^2$ and $Ar^3$ respectively are the same as each other, and in the case where the aromatic rings have substituents, the kinds, the substitution positions, and the number of the substituents substituted on the aromatic rings are the same as each other.

In the general formula (2), $R^1$ to $R^8$ each independently represent a hydrogen atom or a substituent. All $R^1$ to $R^8$ may be hydrogen atoms. In the case where two or more thereof are substituents, the substituents may be the same as or different from each other. Examples of the substituent that may be represented by $R^1$ to $R^8$ include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, a substituted or unsubstituted alkoxy group having from 1 to 20 carbon atoms, a substituted or unsubstituted aryl group having from 6 to 40 carbon atoms, a substituted or unsubstituted heteroaryl group having from 3 to 40 carbon atoms, and a dialkyl-substituted amino group having from 1 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

Among these substituents, $R^1$ to $R^6$ each preferably represent a substituent represented by the general formula (2), an alkyl group having from 1 to 6 carbon atoms, an aryl group having from 6 to 14 carbon atoms, or an aralkyl group having from 7 to 15 carbon atoms.

The alkyl group referred in the description herein may be linear, branched or cyclic, and more preferably has from 1 to 6 carbon atoms, and specific examples thereof include a methyl group, an ethyl group, a propyl group, a butyl group, a tert-butyl group, a pentyl group, a hexyl group, and an isopropyl group. The aryl group may be a monocyclic ring or a condensed ring, and specific examples thereof include a phenyl group and a naphthyl group. The alkoxy group may be linear, branched or cyclic, and more preferably has from 1 to 6 carbon atoms, and specific examples thereof include a methoxy group, an ethoxy group, a propoxy group, a butoxy group, a tert-butoxy group, a pentyloxy group, a hexyloxy group, and an isopropoxy group. The two alkyl groups of the dialkylamino group may be the same as or different from each other, and are preferably the same as each other. The two alkyl groups of the dialkylamino group each independently may be linear, branched or cyclic, and more preferably have from 1 to 6 carbon atoms, and specific examples thereof include a methyl group, an ethyl group, a propyl group, a butyl group, a pentyl group, a hexyl group, and an isopropyl group. The two alkyl groups of the dialkylamino group may be bonded to form a cyclic structure along with the nitrogen atom of the amino group. The aryl group that may be used as the substituent may be a monocyclic ring or a fused ring, and specific examples thereof include a phenyl group and a naphthyl group. The heteroaryl group may be a monocyclic ring or a fused ring, and specific examples thereof include a pyridyl group, a pyridazyl group, a pyrimidyl group, a triazyl group, a triazolyl group, and a benzotriazolyl group. The heteroaryl group may be a group that is bonded through the hetero atom or a group that is bonded through the carbon atom constituting the heteroaryl ring. Two aryl groups of the diarylamino group each may be a monocyclic ring or a fused ring, and specific examples thereof include a phenyl group and a naphthyl group. Two aryl groups of the diarylamino group may be bonded to each other to form a cyclic structure along with the nitrogen atom of the amino group, and examples thereof include a 9-carbazolyl group.

In the general formula (2), $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure. The cyclic structure may be an aromatic ring or an aliphatic ring, and may contain a heteroatom, and the cyclic structure may be a condensed ring containing two or more rings. The hetero atom referred herein is preferably selected from a group consisting of a nitrogen atom, an oxygen atom, and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring, and a cycloheptene ring.

In the general formula (2), Z represents O, S, $R^9$—N, $(R^{10})(R^{11})C$, or $(R^{12})(R^{13})Si$, and $R^9$ to $R^{13}$ each independently represent a hydrogen atom or a substituent. For the descriptions and the preferred ranges of the substituent that may be represented by $R^9$ to $R^{13}$, reference may be made to the descriptions and the preferred ranges of the substituent that may be represented by $R^1$ to $R^8$.

The group represented by the general formula (2) is preferably a group having a structure represented by the following general formula (3), a group having a structure represented by the following general formula (4), a group having a structure represented by the following general formula (5), a group having a structure represented by the following general formula (6), or a group having a structure represented by the following general formula (7).

General Formula (3)

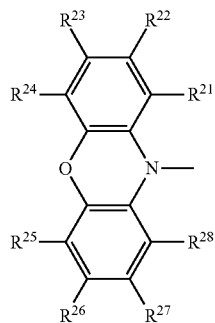

General Formula (4)

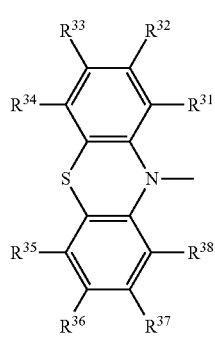

General Formula (5)

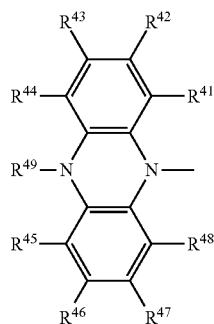

General Formula (6)

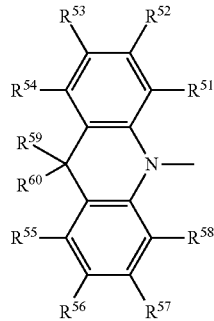

General Formula (7)

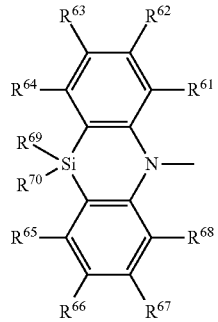

In the general formulae (3) to (7), $R^{21}$ to $R^{28}$, $R^{31}$ to $R^{38}$, $R^{41}$ to $R^{49}$, $R^{51}$ to $R^{60}$, and $R^{61}$ to $R^{70}$ each independently represent a hydrogen atom or a substituent. For the descriptions and the preferred ranges of the substituent that may be represented by $R^{21}$ to $R^{26}$, $R^{31}$ to $R^{38}$, $R^{41}$ to $R^{49}$, $R^{51}$ to $R^{60}$, and $R^{61}$ to $R^{70}$, reference may be made to the descriptions and the preferred ranges of the substituent that may be represented by $R^1$ to $R^8$.

The number of the substituents in the general formulae (3) to (7) is not limited, and all $R^{21}$ to $R^{28}$, $R^{31}$ to $R^{38}$, $R^{41}$ to $R^{49}$, $R^{51}$ to $R^{60}$, and $R^{61}$ to $R^{70}$ may be unsubstituted (i.e., hydrogen atoms). In the case where there are two or more substituents in the general formulae (3) to (7), the substituents may be the same as or different from each other. In the case where the general formulae (3) to (7) have a substituent, the substituent is preferably any of $R^{22}$ to $R^{27}$ for the general formula (3), any of $R^{32}$ to $R^{37}$ for the general formula (4), any of $R^{42}$ to $R^{47}$ and $R^{49}$ for the general formula (5), any of $R^{52}$, $R^{53}$, $R^{56}$, $R^{57}$, $R^{59}$, and $R^{60}$ for the general formula (6), and any of $R^{62}$, $R^{63}$, $R^{66}$, $R^{67}$, $R^{69}$, and $R^{70}$ for the general formula (7).

In the general formulae (3) to (7), $R^{21}$ and $R^{22}$, $R^{22}$ and $R^{23}$, $R^{23}$ and $R^{24}$, $R^{25}$ and $R^{26}$, $R^{26}$ and $R^{27}$, $R^{27}$ and $R^{28}$, $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{59}$ and $R^{60}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, and $R^{69}$ and $R^{70}$ each may be bonded to each other to form a cyclic structure. For the descriptions and the preferred ranges of the cyclic structure, reference may be made to the corresponding descriptions in the general formula (2).

The groups represented by the general formulae (3) to (5) present in the general formula (1) are preferably groups that are represented by any one of the general formulae (3) to (5). Preferred examples thereof include a case where the group is a group represented by the general formula (3), and a case where all the group are represented by the general formula (4).

The compound represented by the general formula (1) preferably has a structure represented by the following general formula (8):

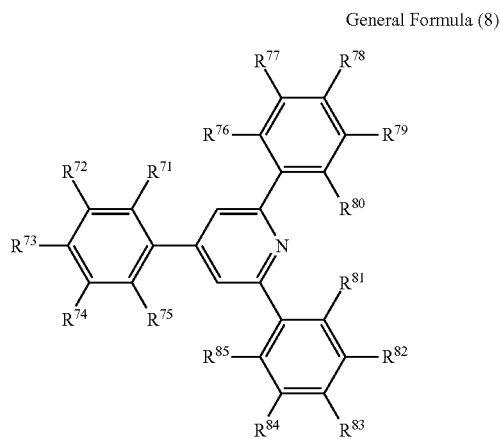

General Formula (8)

In the general formula (8), at least one of $R^{71}$ to $R^{85}$ represents a group represented by the general formula (2); and the other thereof each independently represent a hydrogen atom or a substituent other than a substituent represented by the general formula (2).

In the general formula (8), at least one of $R^{71}$ to $R^{85}$ represents a group represented by the general formula (2), and the number of the substituent represented by the general formula (2) is preferably from 1 to 9, and more preferably from 1 to 6, among $R^{71}$ to $R^{85}$. For example, the number of the substituent may be selected from a range of from 1 to 3. The group represented by the general formula (2) may be bonded to each of the three benzene rings bonded to the pyridine ring, or may be only one or two benzene rings. Preferred examples thereof include a case where the three benzene rings each have from 0 to 3 of the group represented by the general formula (2), and more preferred examples thereof include a case where the three benzene rings each have from 0 to 2 of the group represented by the general formula (2). For example, a case where the three benzene rings each have 0 or 1 of the group represented by the general formula (2) may be selected.

The substitution position of the group represented by the general formula (2) may be any of $R^{71}$ to $R^{85}$, and the substitution position is preferably selected from $R^{72}$ to $R^{74}$, $R^{77}$ to $R^{79}$, and $R^{82}$ to $R^{84}$. Examples thereof include a case where from 0 to 2 of $R^{72}$ to $R^{74}$, from 0 to 2 of $R^{77}$ to $R^{79}$, and from 0 to 2 of $R^{82}$ to $R^{84}$ each represent the group represented by the general formula (2), and a case where 0 or 1 of $R^{72}$ to $R^{74}$, 0 or 1 of $R^{77}$ to $R^{79}$, and 0 or 1 of $R^{82}$ to $R^{84}$ each represent the group represented by the general formula (2).

In the case where any one of $R^{71}$ to $R^{85}$ is substituted by the group represented by the general formula (2), the substitution position thereof is preferably $R^{73}$. In the case where any two of $R^{71}$ to $R^{85}$ are substituted by the substituent represented by the general formula (2), the substitution positions thereof are preferably $R^{76}$ and $R^{83}$. In the case where any three of $R^{71}$ to $R^{85}$ are substituted by the group represented by the general formula (2), the substitution positions thereof are preferably $R^{73}$, $R^{78}$, and $R^{83}$.

Among $R^{71}$ to $R^{85}$, ones that do not represent the substituent represented by the general formula (2) each independently represent a hydrogen atom or a substituent other than a substituent represented by the general formula (2), and may be all hydrogen atoms. In the case where two or more of them are the substituents, the substituents may be different from each other within each of $R^{71}$ to $R^{75}$, $R^{76}$ to $R^{80}$, and $R^{81}$ to $R^{85}$, and may be different from each other between $R^{71}$ to $R^{75}$ and $R^{76}$ to $R^{80}$ or between $R^{71}$ to $R^{75}$ and $R^{81}$ to $R^{85}$, but are the same as each other between $R^{76}$ to $R^{80}$ and $R^{81}$ to $R^{85}$. Specifically, $R^{76}$ and $R^{81}$ are the same as each other, $R^{77}$ and $R^{82}$ are the same as each other, $R^{78}$ and $R^{83}$ are the same as each other, $R^{79}$ and $R^{84}$ are the same as each other, and $R^{80}$ and $R^{85}$ are the same as each other. For the descriptions and the preferred ranges of the substituent that may be represented by $R^{71}$ to $R^{85}$, reference may be made to the descriptions and the preferred ranges of the substituent that may be represented by $R^1$ to $R^8$.

In the general formula (8), $R^{71}$ and $R^{72}$, $R^{72}$ and $R^{73}$, $R^{73}$ and $R^{74}$, $R^{74}$ and $R^{75}$, $R^{76}$ and $R^{77}$, $R^{77}$ and $R^{78}$, $R^{78}$ and $R^{79}$, $R^{79}$ and $R^{80}$, $R^{81}$ and $R^{82}$, $R^{82}$ and $R^{83}$, $R^{83}$ and $R^{84}$, and $R^{84}$ and $R^{85}$ each may be bonded to each other to form a cyclic structure. For the descriptions and the preferred ranges of the cyclic structure, reference may be made to the corresponding descriptions in the general formula (2).

The group represented by the general formula (2) contained in the general formula (8) is preferably a group having a structure represented by the general formula (3), a group having a structure represented by the general formula (4), a group having a structure represented by the general formula (5), a group having a structure represented by the general formula (6), or a group having a structure represented by the general formula (7).

The compound represented by the general formula (8) may have a molecular structure that is or is not symmetric. For example, the compound may have or may not have a rotation symmetric structure with the center of the pyridine ring as the axis.

Specific examples of the compound represented by the general formula (1) shown below. However, the compound represented by the general formula (1) capable of being used in the invention is not construed as being limited to the specific examples.

Compound 1
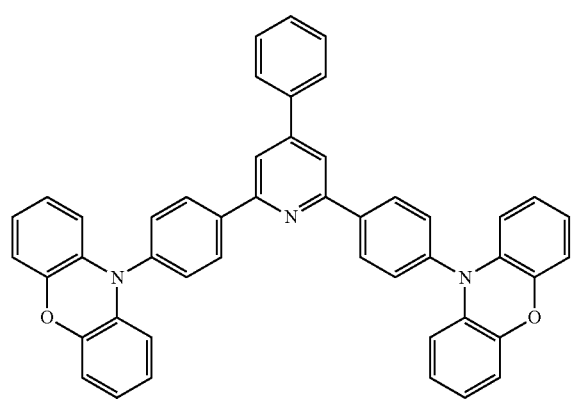
Compound 2
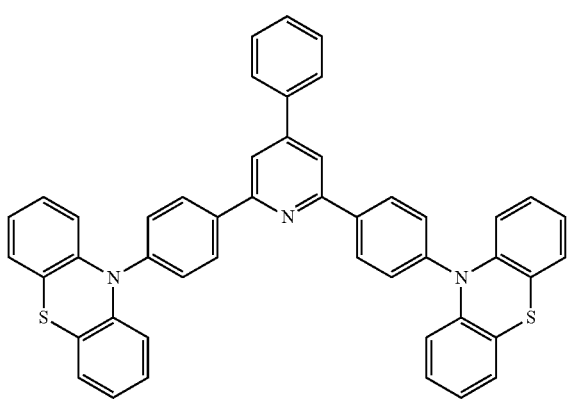
Compound 3
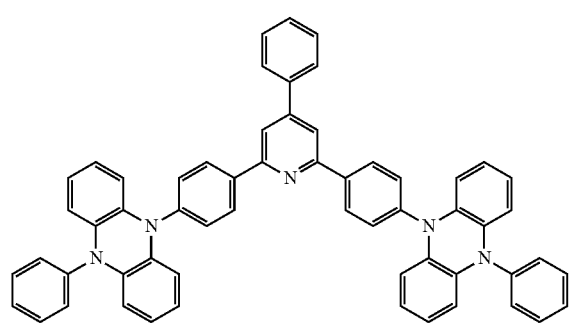
Compound 4
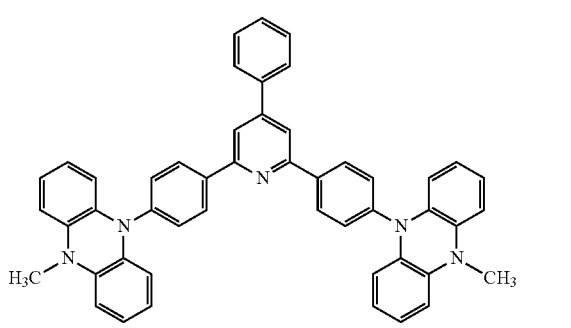
Compound 5
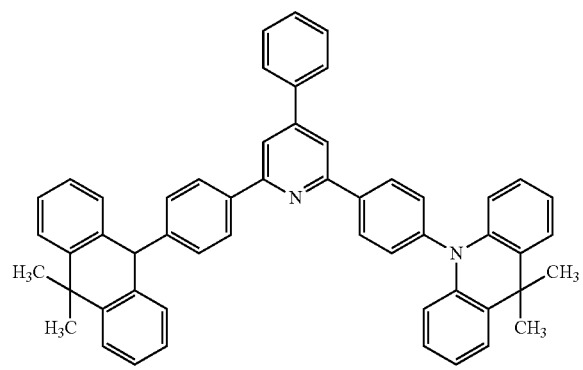
Compound 6
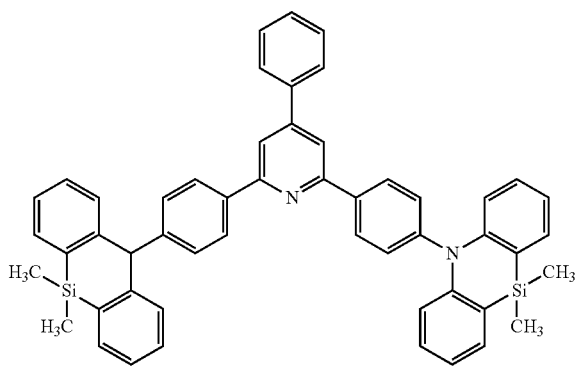
Compound 7
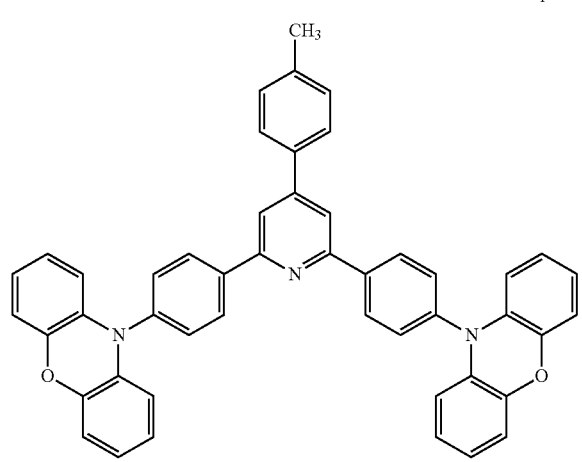
Compound 8
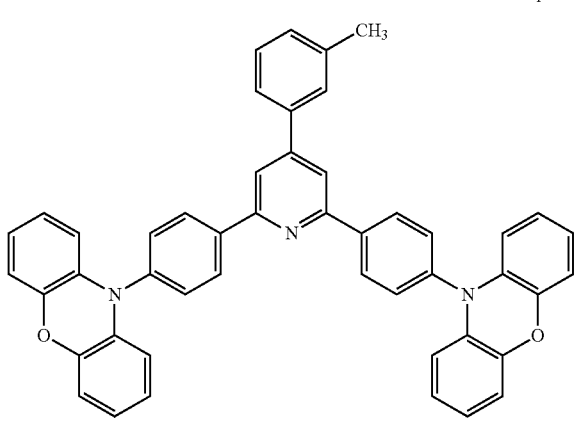

-continued
Compound 9
Compound 10
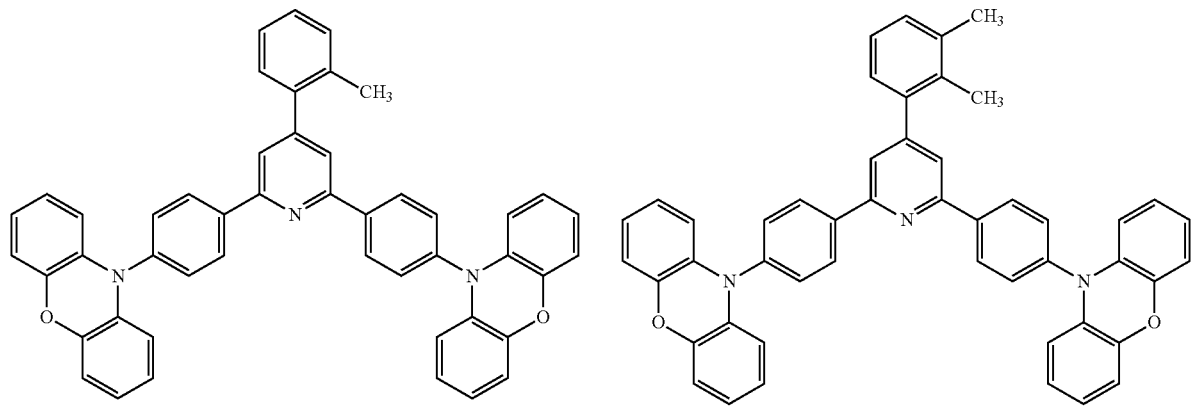
Compound 11
Compound 12
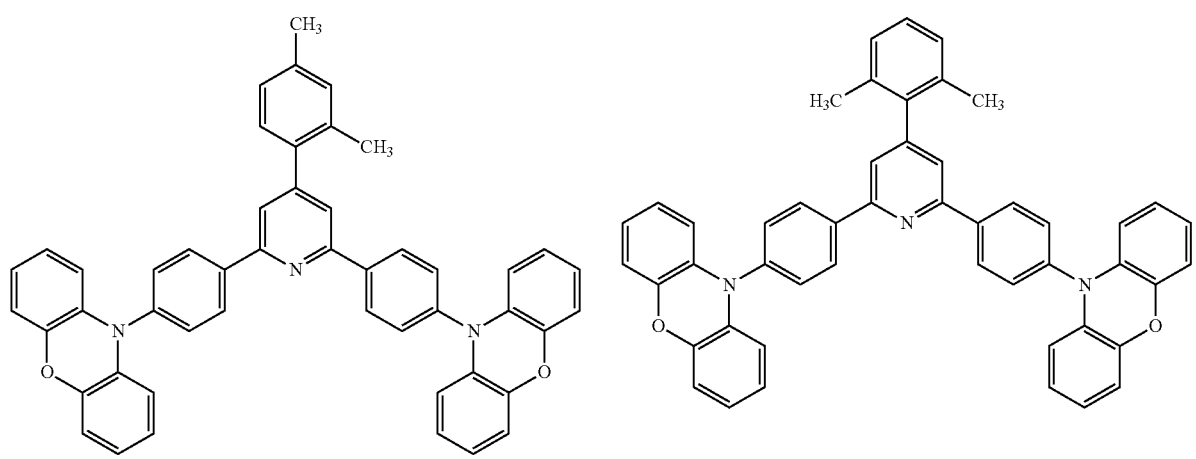
Compound 13
Compound 14
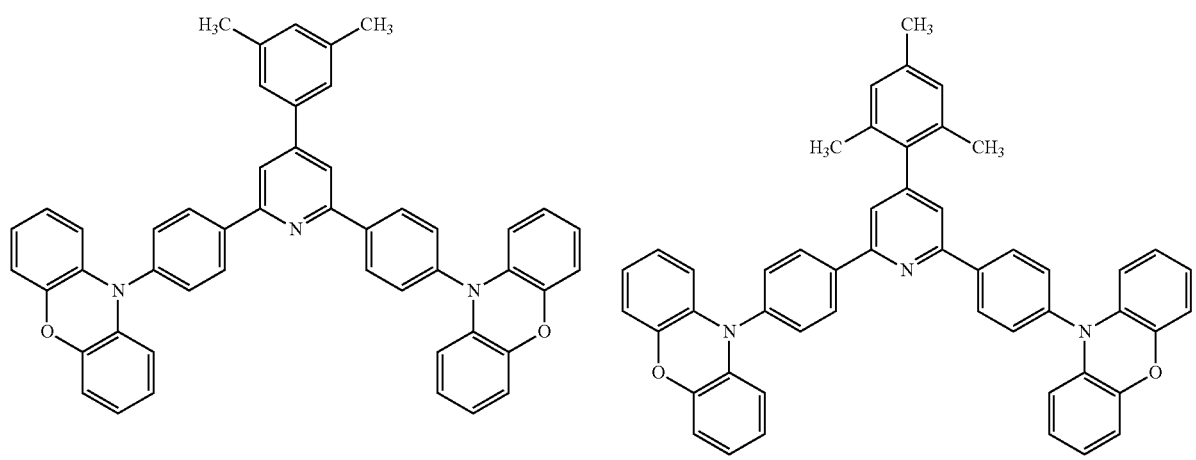

-continued
Compound 15
Compound 16
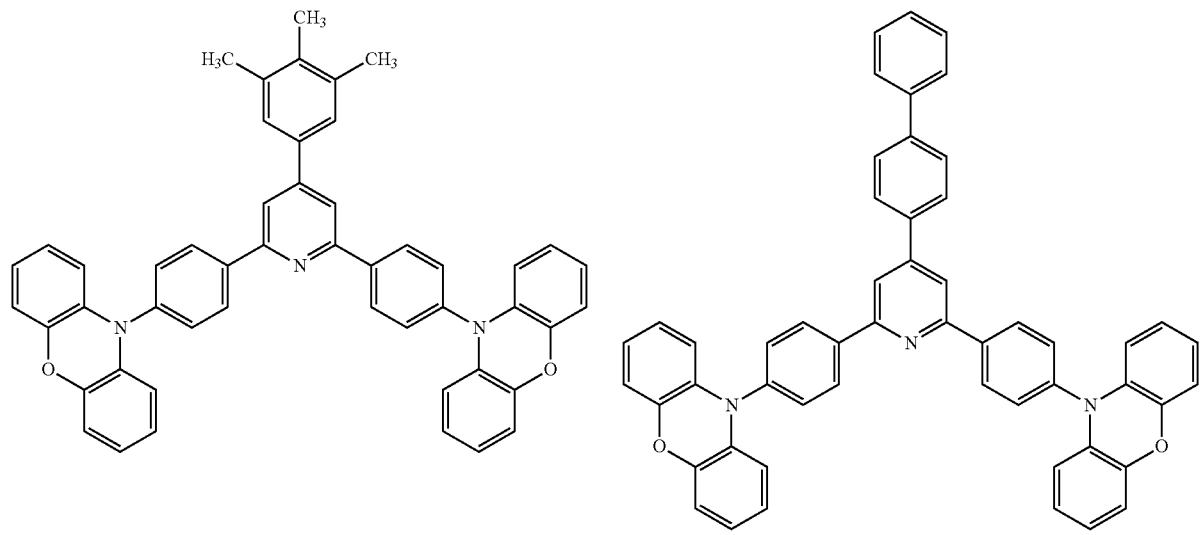
Compound 17
Compound 18
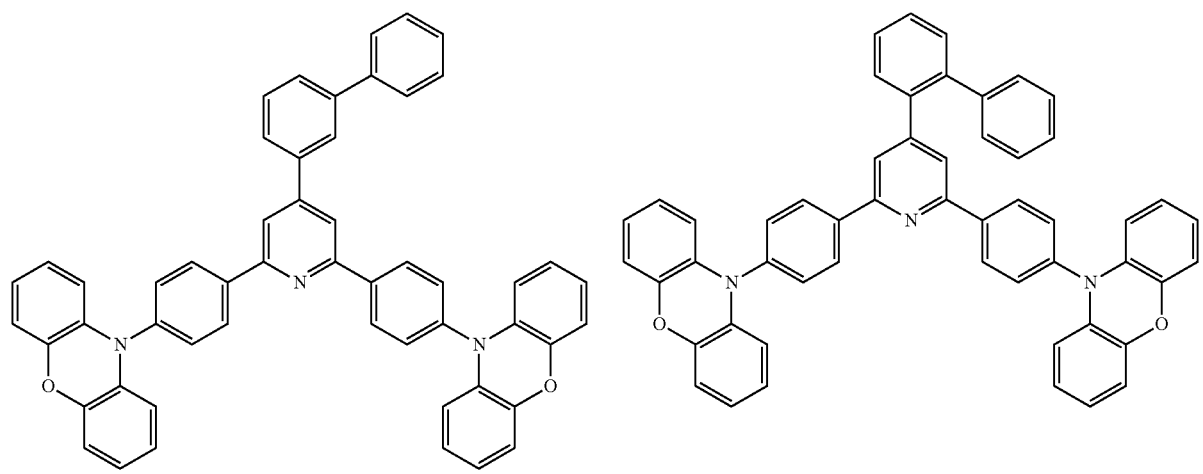
Compound 19
Compound 20
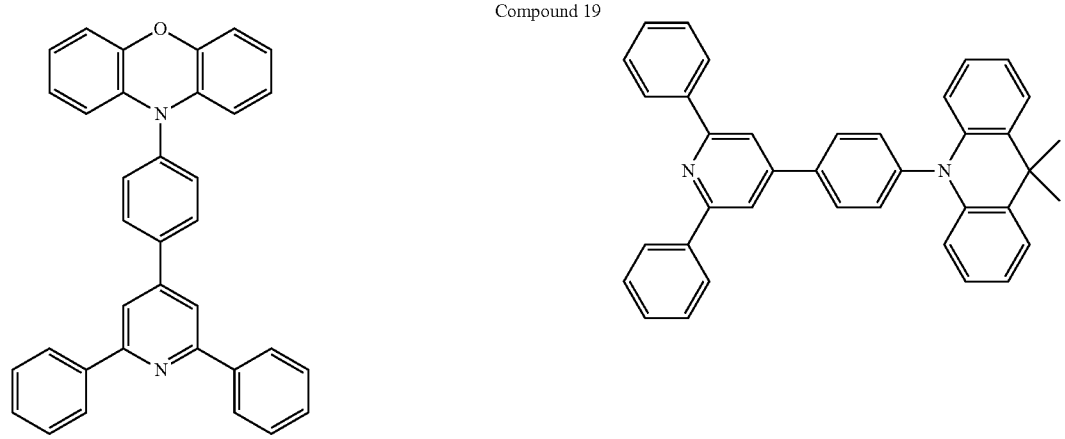

-continued

Compound 21

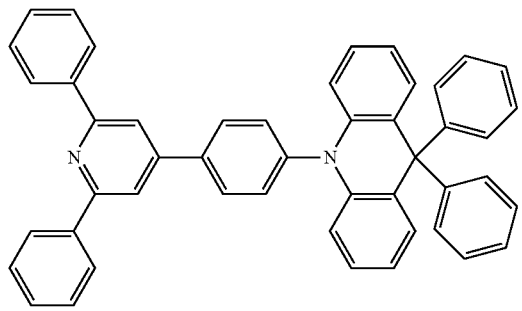

Compound 22

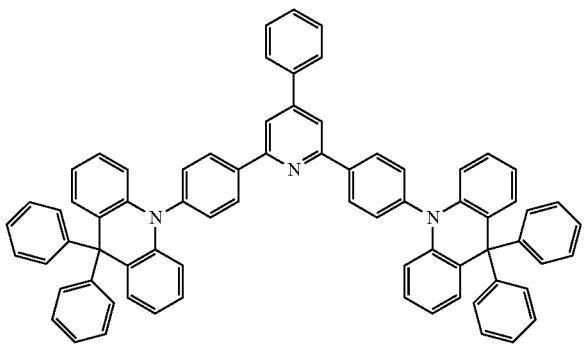

Compound 23

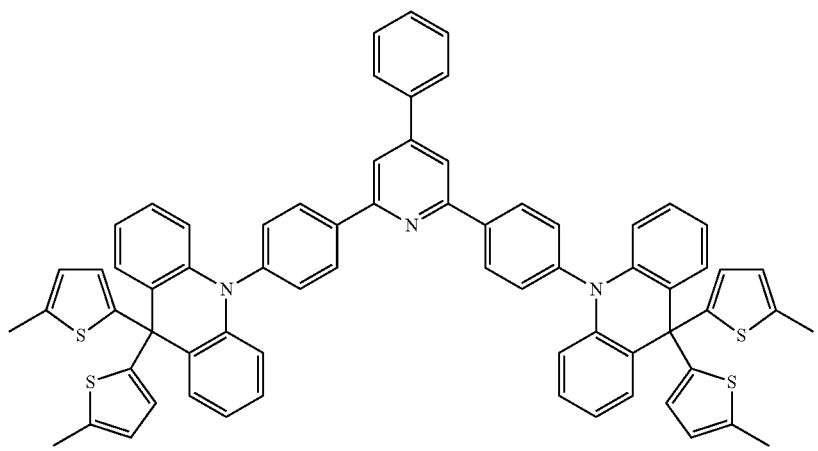

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method and used. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light emitting material.

For example, it may be considered that a polymerizable group is introduced in advance to the structure represented by the general formula (1), and a polymer obtained by polymerizing the polymerizable group is used as a light emitting material. Specifically, it may be considered that a monomer that has a polymerizable functional group at any of $Ar^1$ to $Ar^3$ in the general formula (1) is prepared, and is homopolymerized or copolymerized with another monomer to prepare a polymer containing repeating units, and the polymer is used as a light emitting material. In alternative, it may be considered that the compounds represented by the general formula (1) are reacted to form a dimer or a trimer, and the dimer or the trimer is used as a light emitting material.

Examples of the polymer having the repeating unit containing the structure represented by the general formula (1) include a polymer containing a structure represented by the following general formula (9) or (10).

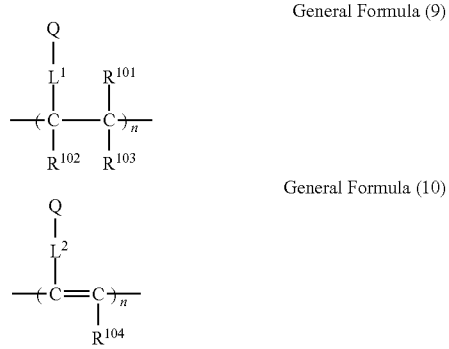

General Formula (9)

General Formula (10)

In the general formulae (9) and (10), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by —$X^{11}$-$L^{11}$-, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (9) and (10), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $Ar^1$ to $Ar^3$ of the structure of the general formula (1) constituting Q. Two or more of the linking groups may be boded to one group represented by Q to form a crosslinked structure or a network structure.

Specific examples of the structure of the repeating unit include structures represented by the following formulae (11) to (14).

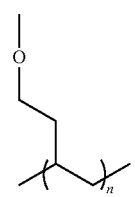

Formula (11)

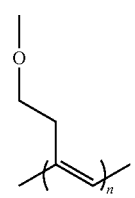

Formula (12)

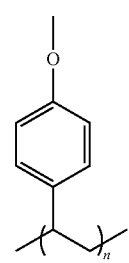

Formula (13)

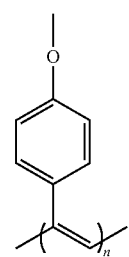

Formula (14)

The polymer having the repeating unit containing the structure represented by any of the formulae (11) to (14) may be synthesized in such a manner that a hydroxyl group is introduced to at least one of the substituents of $Ar^1$ to $Ar^3$ of the general formula (1), and the hydroxyl group as a linker is reacted with the following compound to introduce a polymerizable group thereto, followed by polymerizing the polymerizable group.

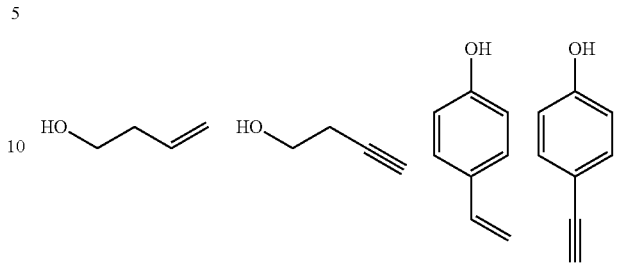

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene, but the invention is not limited to the repeating units shown herein.

Synthesis Method of Compound Represented by General Formula (1)

The compound represented by the general formula (1) may be synthesized by combining the known reactions. For example, the compound represented by the general formula (1), in which $Ar^2$ and $Ar^3$ each represent an aryl group substituted with a group represented by the general formula (2) may be synthesized through reaction of a compound represented by the general formula (15) and a compound represented by the general formula (16) according to the following scheme. The reaction itself has been known in the art, and known reaction conditions may be appropriately selected and used. The compound represented by the general formula (16) may be synthesized, for example, by converting the corresponding chloride to an amine, and further converting to a bromide.

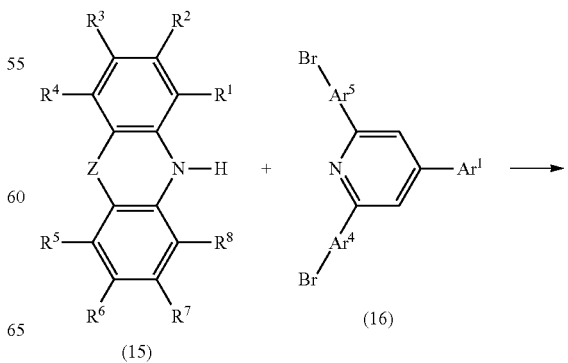

-continued

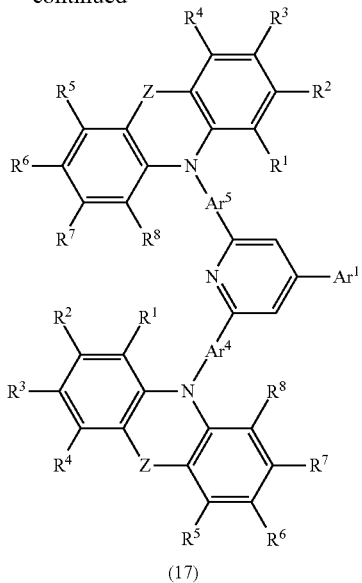

(17)

For the definition of $Ar^1$ in the scheme, reference may be made to the corresponding description in the general formula (1). For the definitions of $R^1$ to $R^8$ and Z, reference may be made to the corresponding descriptions in the general formula (2). In the scheme, $Ar^4$ and $Ar^5$ each independently represent a substituted or unsubstituted arylene group. The aromatic ring constituting the arylene group that may be represented by $Ar^4$ and $Ar^5$ may be a monocyclic ring or a fused ring, and specific examples thereof include a benzene ring, a naphthalene ring, an anthracene ring, and a phenanthrene ring. The arylene group preferably has from 6 to 40 carbon atoms, more preferably from 6 to 20 carbon atoms, and further preferably from 6 to 14 carbon atoms.

The compound that has plural groups represented by the general formula (2) may be synthesized by changing the compound represented by the general formula (16) in the scheme to a compound having plural bromine atoms substituted thereon.

For the detail of the reaction, reference may be made to the synthesis examples described later. The compound represented by the general formula (1) may be synthesized by combining other known synthesis reactions.

Organic Light Emitting Device

The compound represented by the general formula (1) of the invention is useful as a light emitting material of an organic light emitting device. Accordingly, the compound represented by the general formula (1) of the invention may be effectively used as a light emitting material in a light emitting layer of an organic light emitting device. The compound represented by the general formula (1) includes a delayed fluorescent emitter emitting delayed fluorescent light. Thus, the invention provides an invention relating to a delayed fluorescent emitter having the structure represented by the general formula (1), an invention relating to the use of the compound represented by the general formula (1) as the delayed fluorescent emitter, and an invention relating to a method for emitting delayed fluorescent light with the compound represented by the general formula (1). An organic light emitting device that uses the compound as a light emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light emitting material to form an excited state for the light emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy use efficiency. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency.

The use of the compound represented by the general formula (1) of the invention as a light emitting material of a light emitting layer may provide an excellent organic light emitting device, such as an organic photoluminescent device (organic PL device) and an organic electroluminescent device (organic EL device). At this time, the compound represented by the general formula (1) of the invention may have a function of assisting light emission of another light emitting material contained in the light emitting layer, i.e., as a so-called assist dopant. Specifically, the compound represented by the general formula (1) of the invention contained in the light emitting layer may have a lowest excited singlet energy level that is between the lowest excited singlet energy level of the host material contained in the light emitting layer and the lowest excited singlet energy level of the another light emitting material contained in the light emitting layer.

The organic photoluminescent device has a structure containing a substrate having formed thereon at least a light emitting layer. The organic electroluminescent device has a structure containing at least an anode, a cathode and an organic layer formed between the anode and the cathode. The organic layer contains at least a light emitting layer, and may be formed only of a light emitting layer, or may have one or more organic layer in addition to the light emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, denotes a light emitting layer, 6 denotes an electron transporting layer, and 7 denotes a cathode.

The members and the layers of the organic electroluminescent device will be described below. The descriptions for the substrate and the light emitting layer may also be applied to the substrate and the light emitting layer of the organic photoluminescent device.

Substrate

The organic electroluminescent device of the invention is preferably supported by a substrate. The substrate is not particularly limited and may be those that have been commonly used in an organic electroluminescent device, and examples thereof used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-cupper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light Emitting Layer

The light emitting layer is a layer, in which holes and electrons injected from the anode and the cathode, respectively, are recombined to form excitons, and then the layer emits light. A light emitting material may be solely used as the light emitting layer, but the light emitting layer preferably contains a light emitting material and a host material. The light emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light emitting material are confined in the light emitting material. Accordingly, a host material is preferably used in addition to the light emitting material in the light emitting layer. The host material used may be an organic compound that has excited singlet energy and excited triplet energy, at least one of which is higher than those of the light emitting material of the invention. As a result, the singlet excitons and the triplet excitons generated in the light emitting material of the invention are capable of being confined in the molecules of the light emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light emitting device and the organic electroluminescent device of the invention, the light emission occurs in the light emitting material of the invention contained in the light emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light emitting material contained in the light emitting layer is preferably 0.1% by weight or more, and more preferably 1% by weight or more, and is preferably 50% by weight or less, more preferably 20% by weight or less, and further preferably 10% by weight or less.

The host material in the light emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light emitting layer or the hole transporting layer and between the cathode and the light emitting layer or the electron transporting layer. The injection layer may be provided depending on necessity.

Barrier Layer

The barrier layer is a layer that is capable of inhibiting charges (electrons or holes) and/or excitons present in the light emitting layer from being diffused outside the light emitting layer. The electron barrier layer may be disposed between the light emitting layer and the hole transporting layer, and inhibits electrons from passing through the light emitting layer toward the hole transporting layer. Similarly, the hole barrier layer may be disposed between the light emitting layer and the electron transporting layer, and inhibits holes from passing through the light emitting layer toward the electron transporting layer. The barrier layer may also be used for inhibiting excitons from being diffused outside the light emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light emitting layer.

Exciton Barrier Layer

The exciton barrier layer is a layer for inhibiting excitons generated through recombination of holes and electrons in the light emitting layer from being diffused to the charge transporting layer, and the use of the layer inserted enables effective confinement of excitons in the light emitting layer, and thereby enhances the light emission efficiency of the device. The exciton barrier layer may be inserted adjacent to the light emitting layer on any of the side of the anode and the side of the cathode, and on both the sides. Specifically, in the case where the exciton barrier layer is present on the side of the anode, the layer may be inserted between the hole transporting layer and the light emitting layer and adjacent to the light emitting layer, and in the case where the layer is inserted on the side of the cathode, the layer may be inserted between the light emitting layer and the cathode and adjacent to the light emitting layer. Between the anode and the exciton barrier layer that is adjacent to the light emitting layer on the side of the anode, a hole injection layer, an electron barrier layer and the like may be provided, and between the cathode and the exciton barrier layer that is adjacent to the light emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light emitting material, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light emitting layer but also in the other layers than the light emitting layer. In this case, the compound represented by the general formula (1) used in the light emitting layer and the compound represented by the general formula (1) used in the other layers than the light emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_2$ to $R_7$ each independently represent a hydrogen atom or a substituent, and n represents an integer of from 3 to 5.

Preferred examples of a compound that may also be used as the host material of the light emitting layer are shown below.

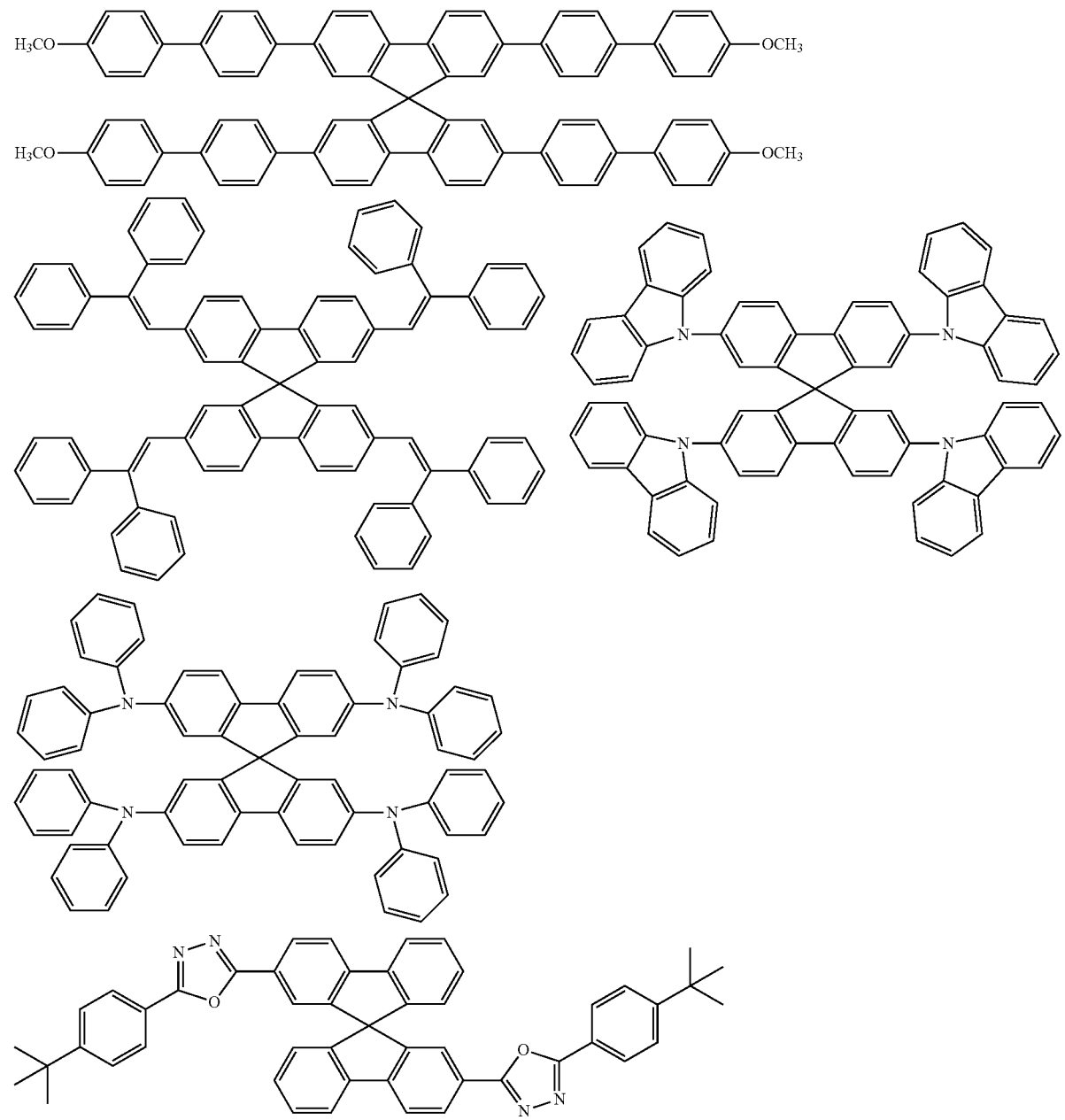

-continued
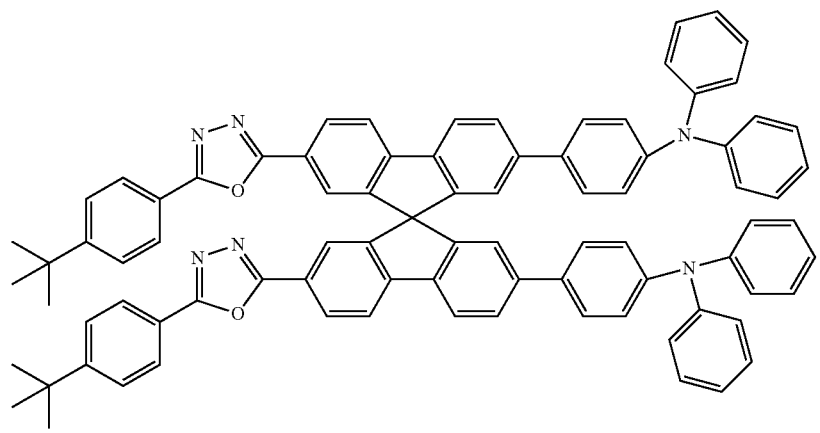
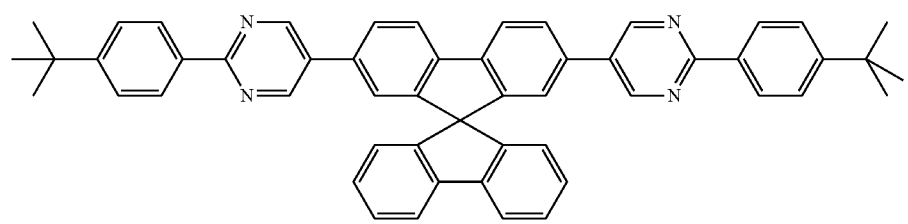
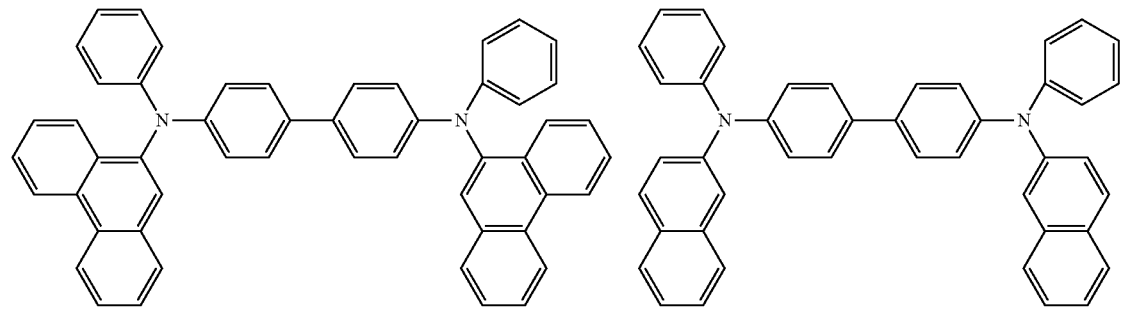
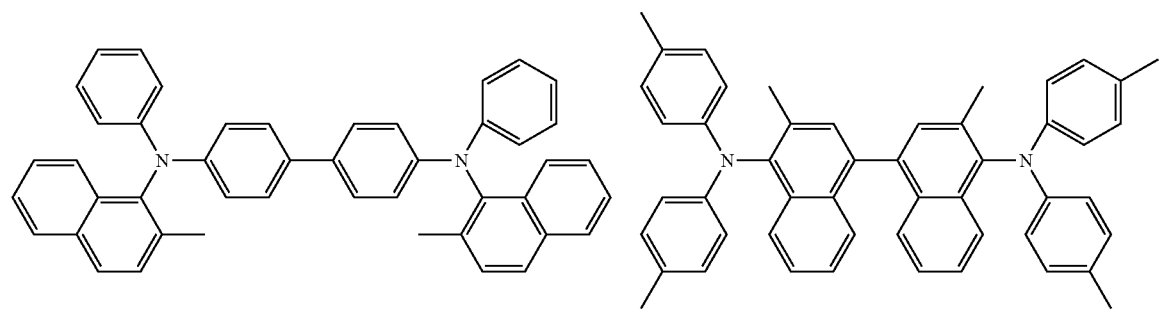

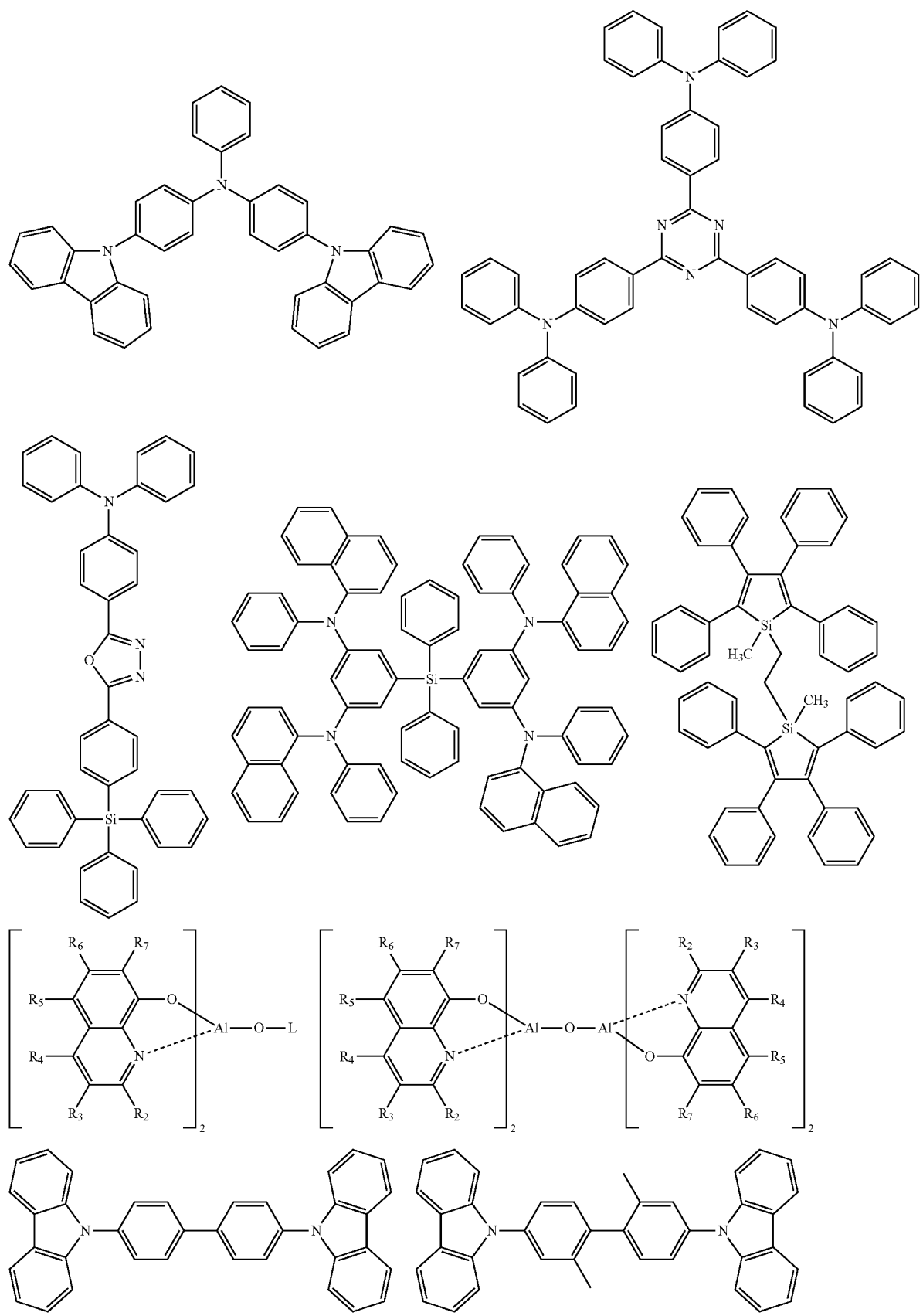

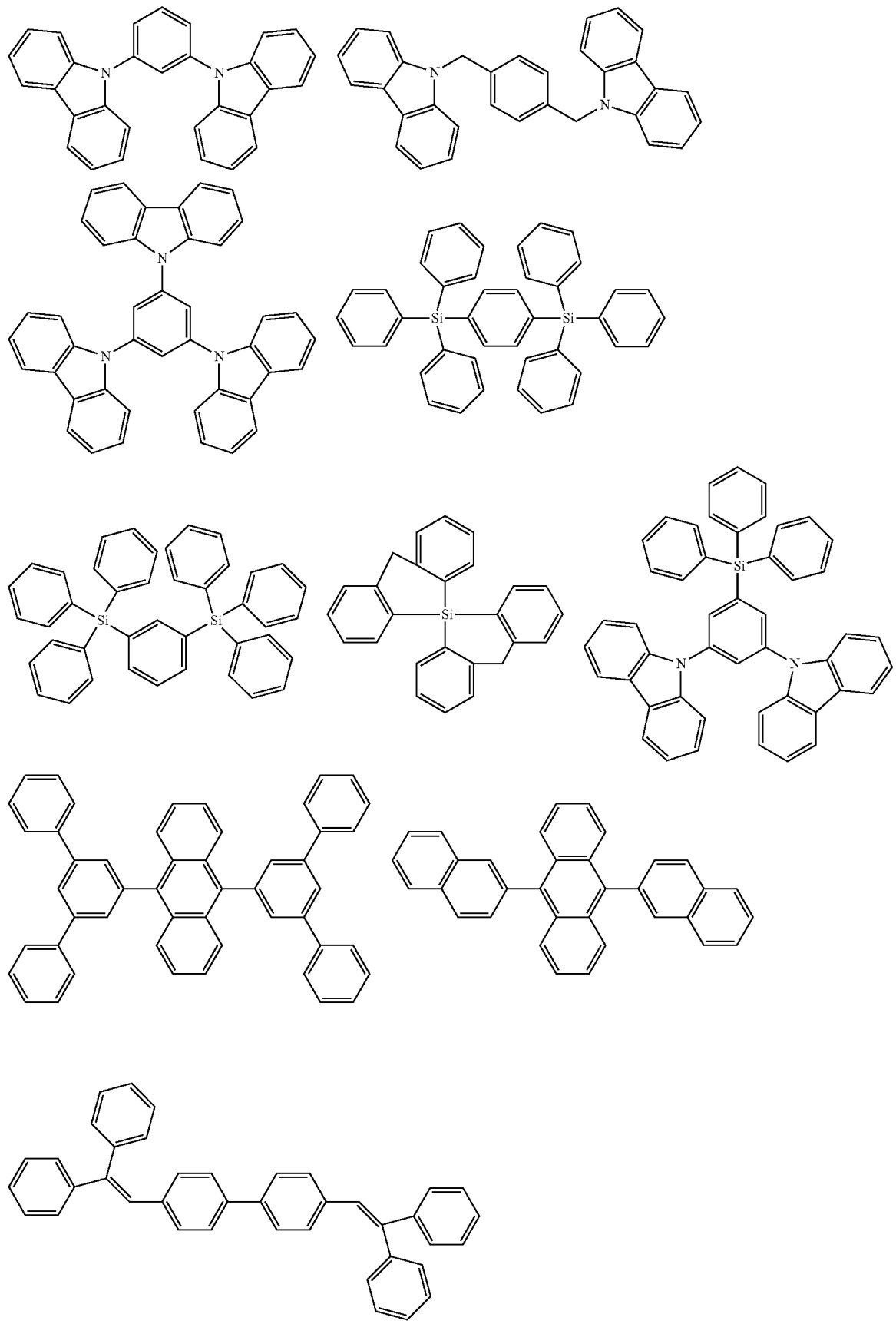

-continued
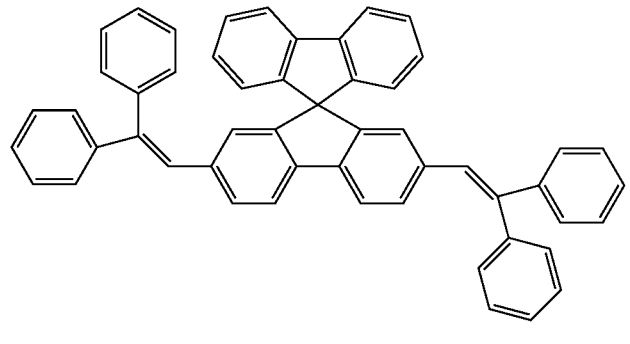
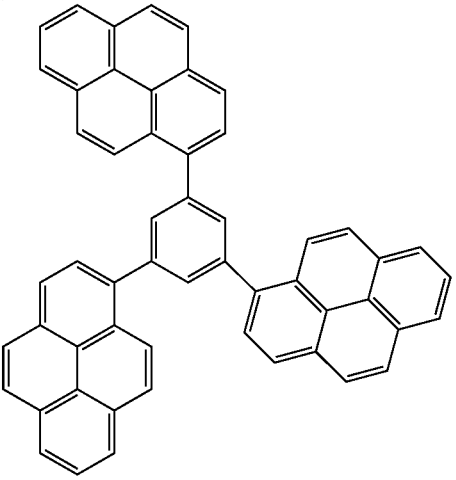
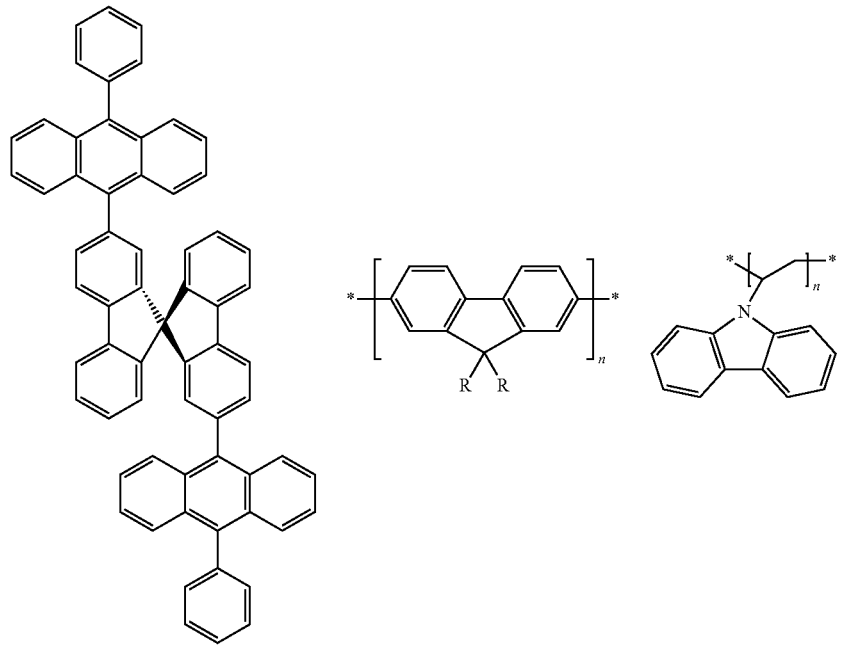
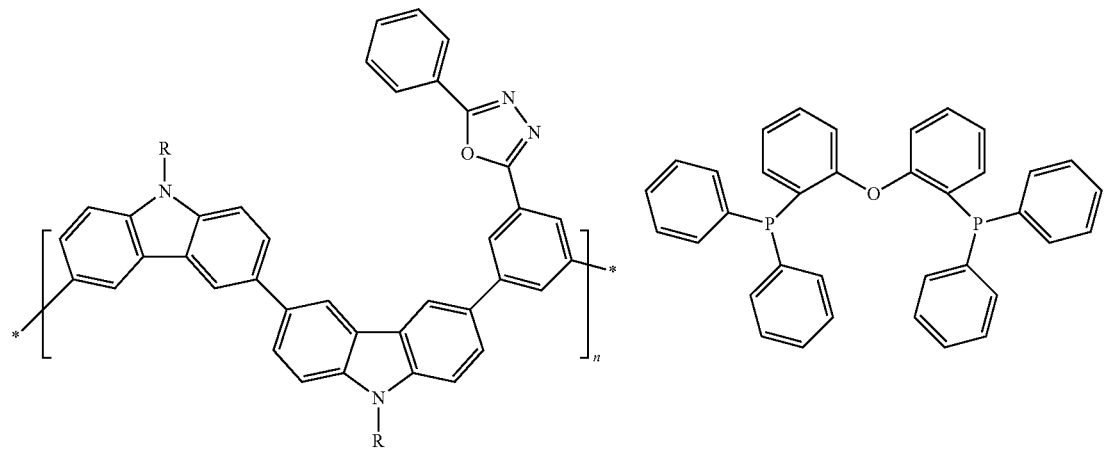

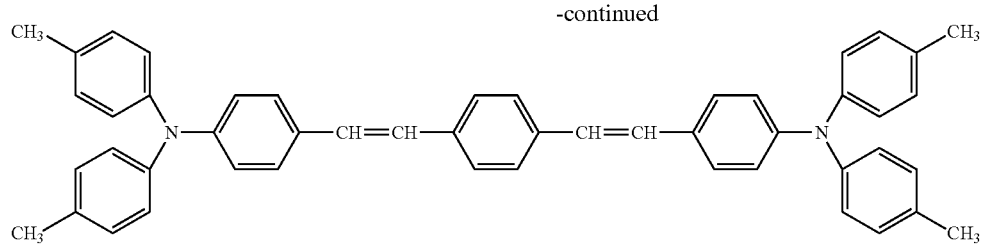
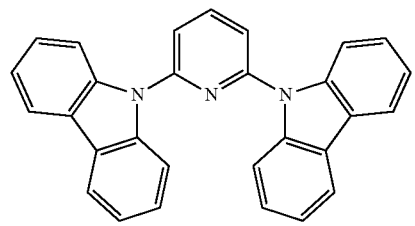
Preferred examples of a compound that may be used as the hole injection material are shown below.
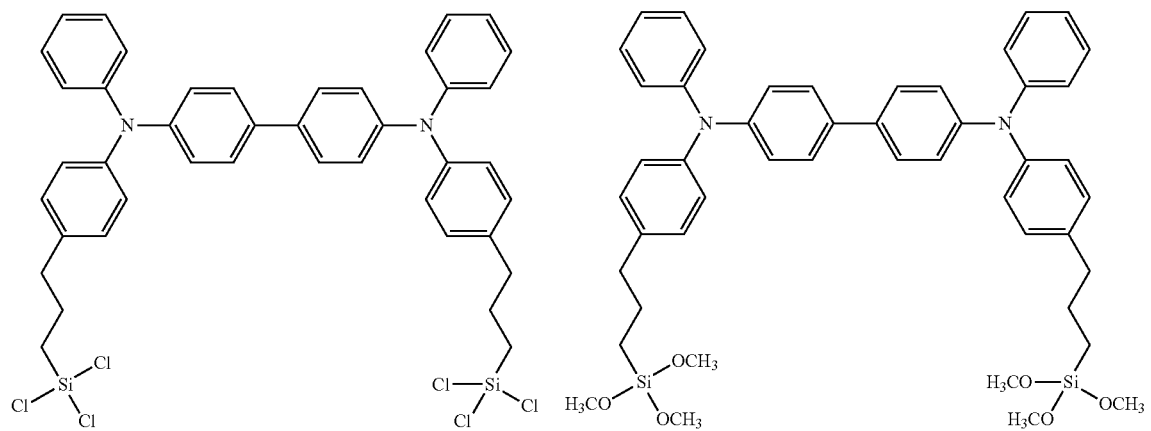
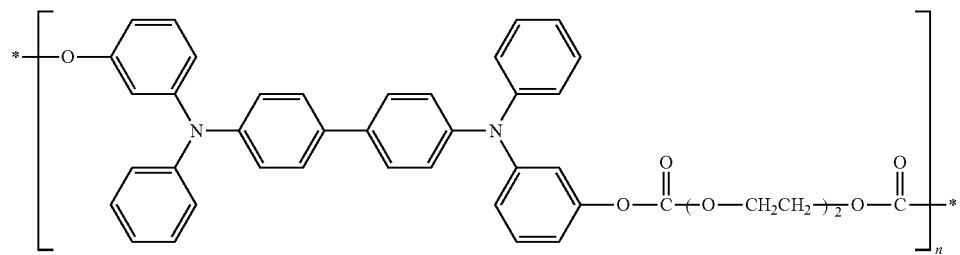

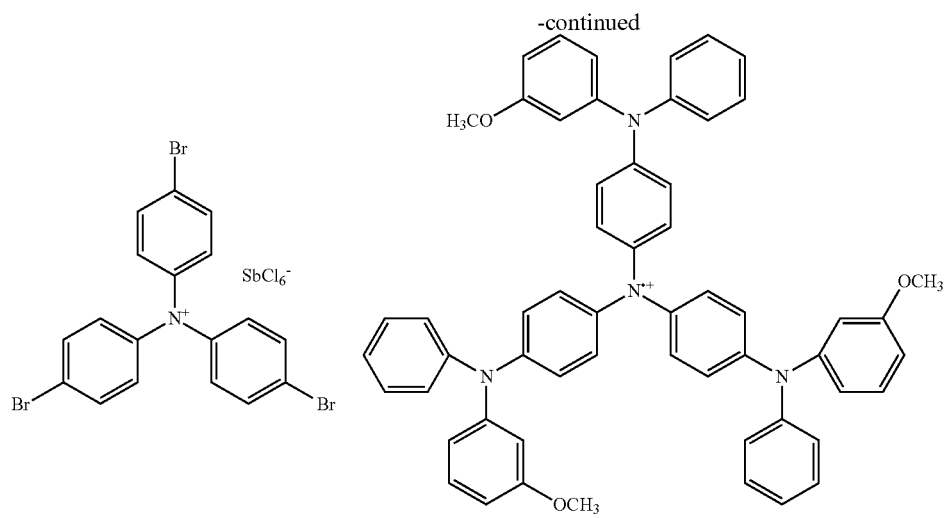
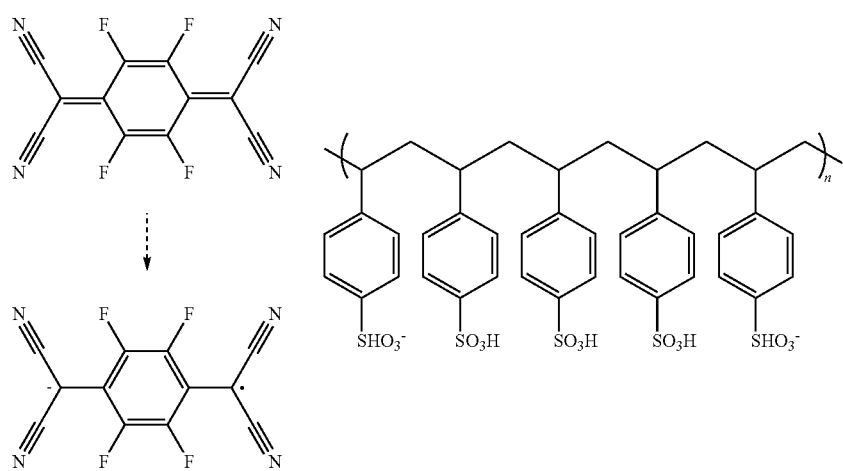
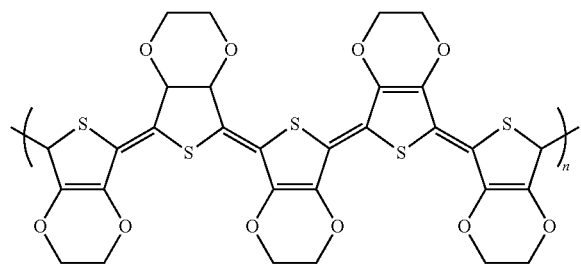
Preferred examples of a compound that may be used as the hole transporting material are shown below.

47 48
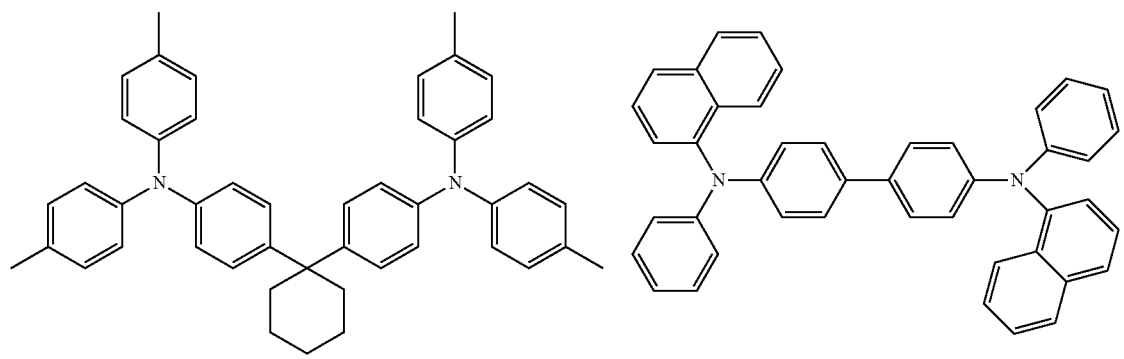
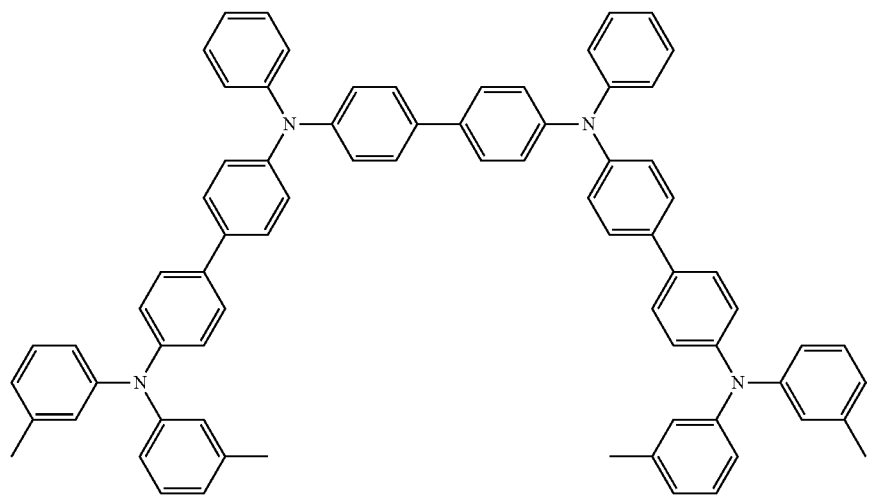
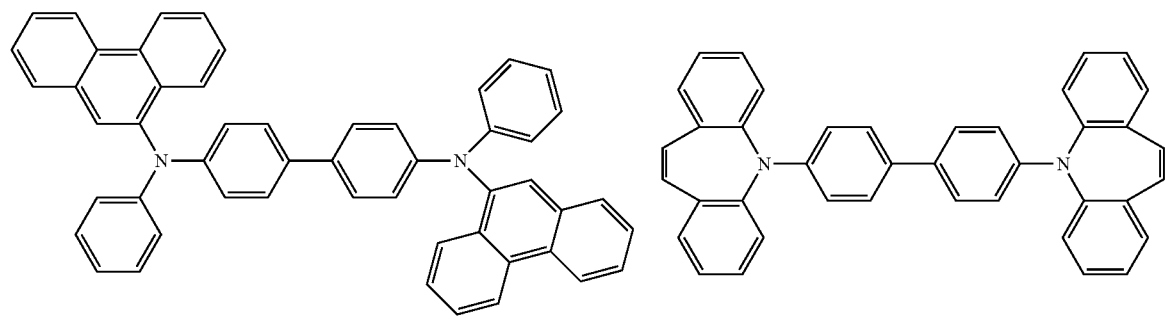

-continued
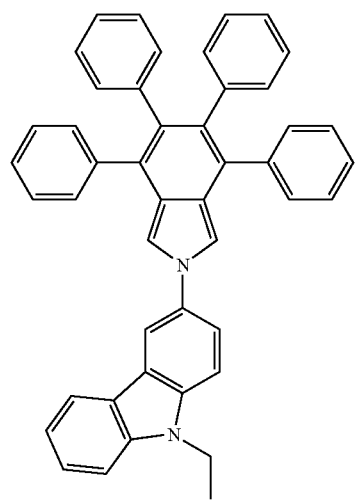
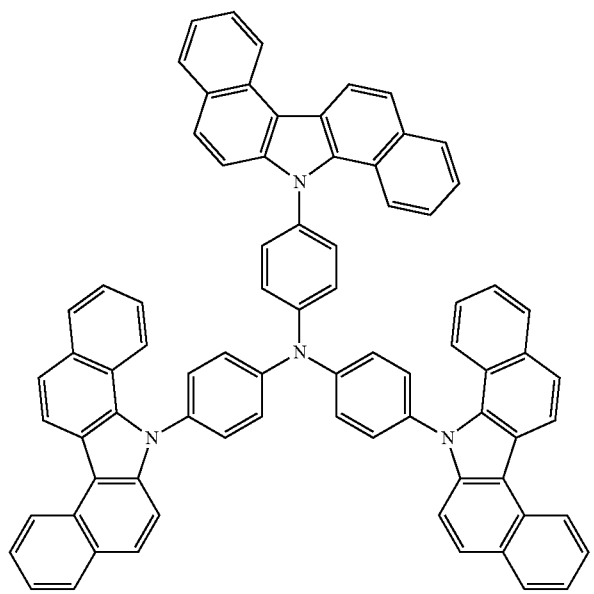
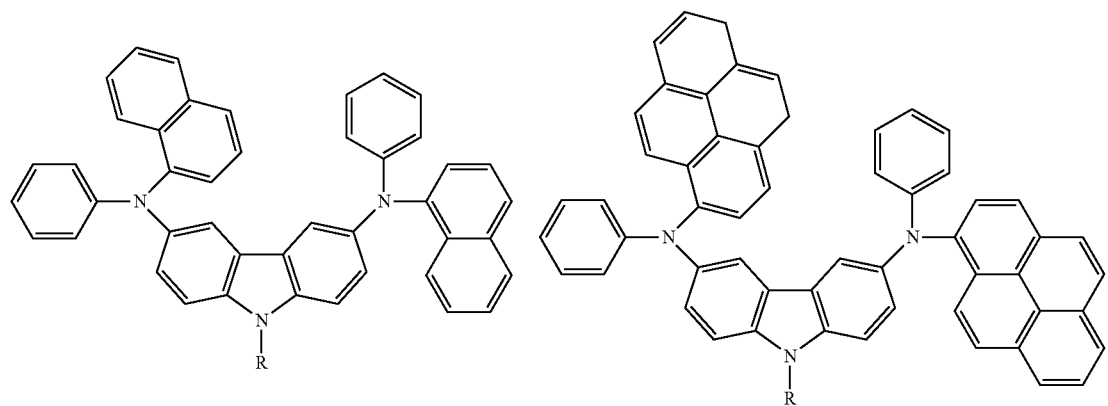
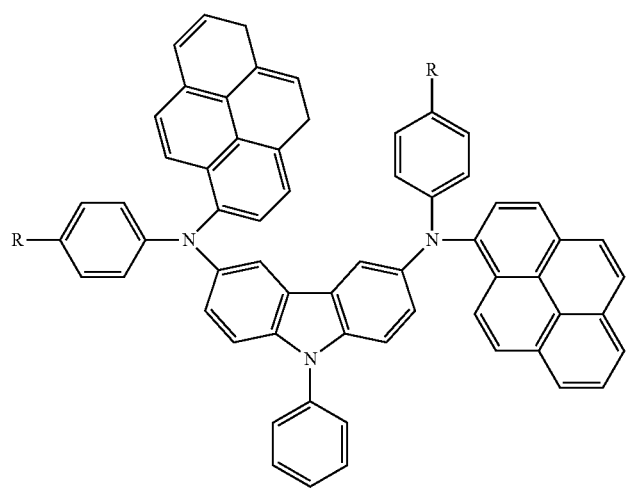

-continued
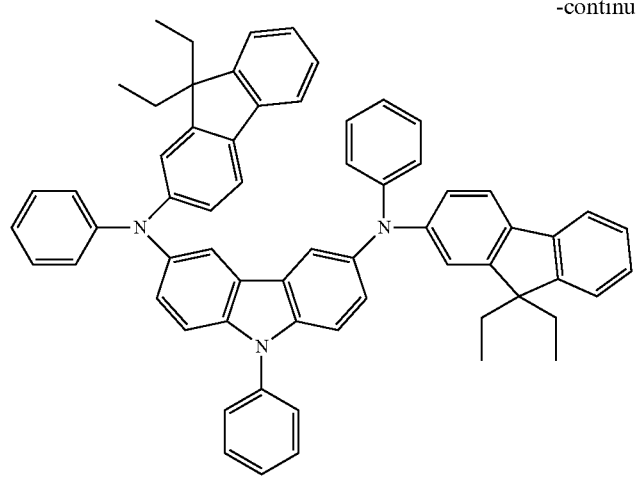
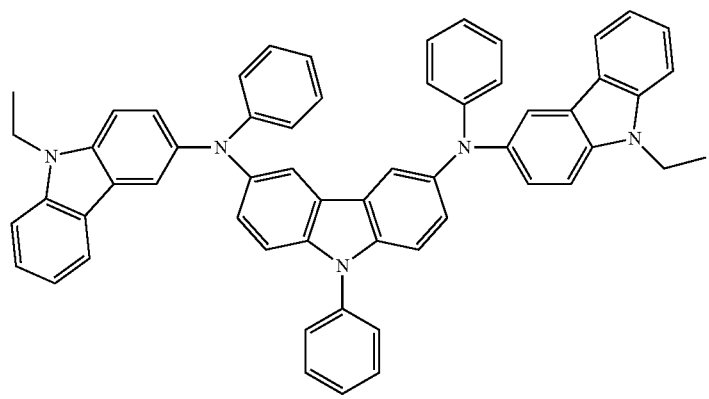
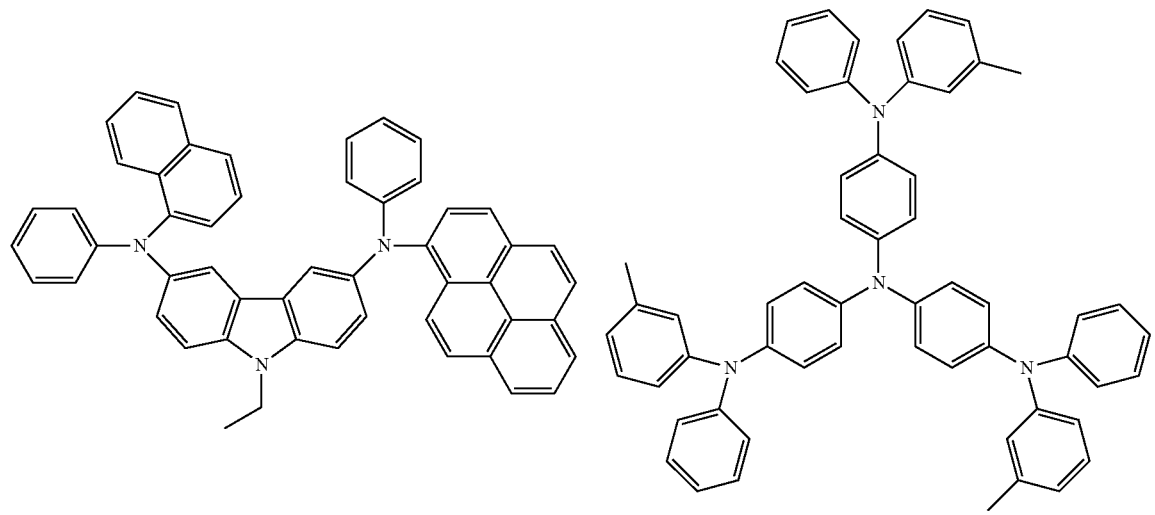

53
54
-continued
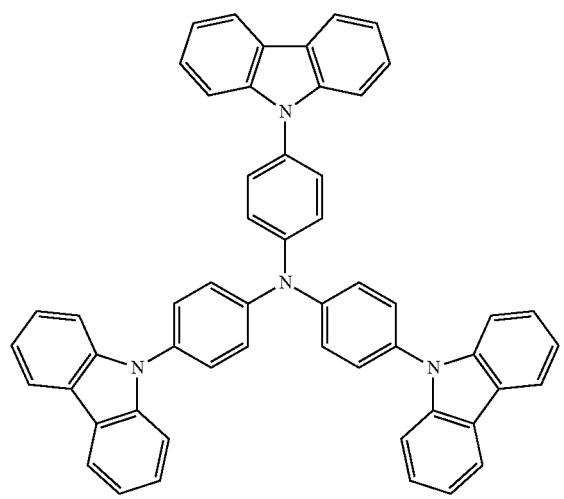
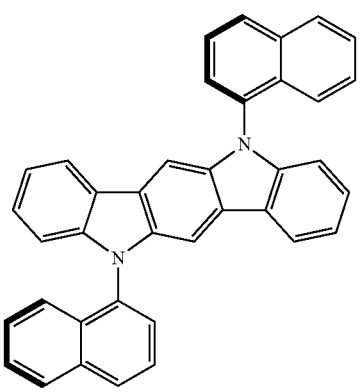
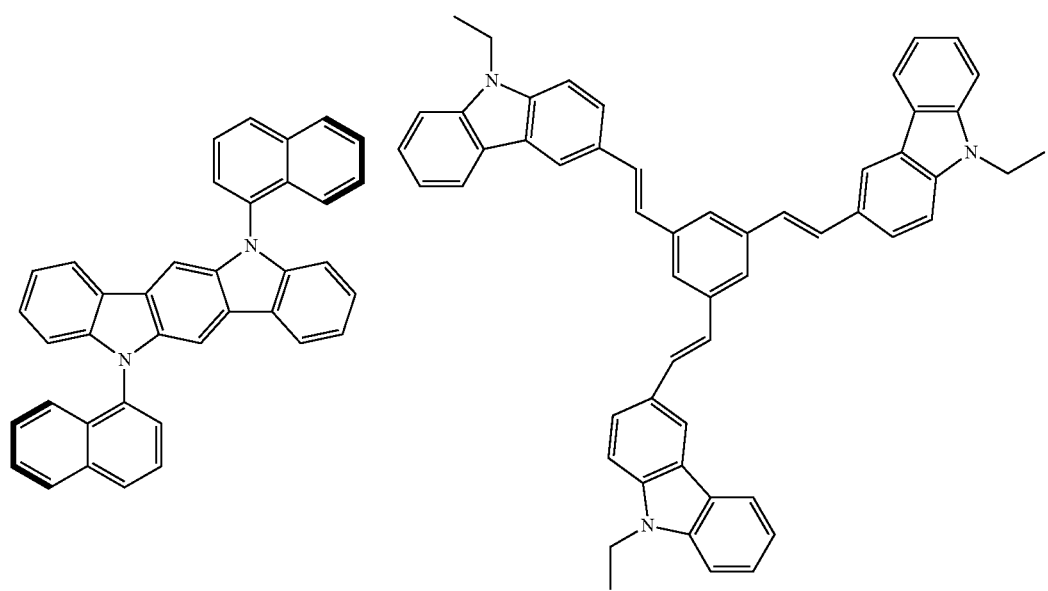

-continued
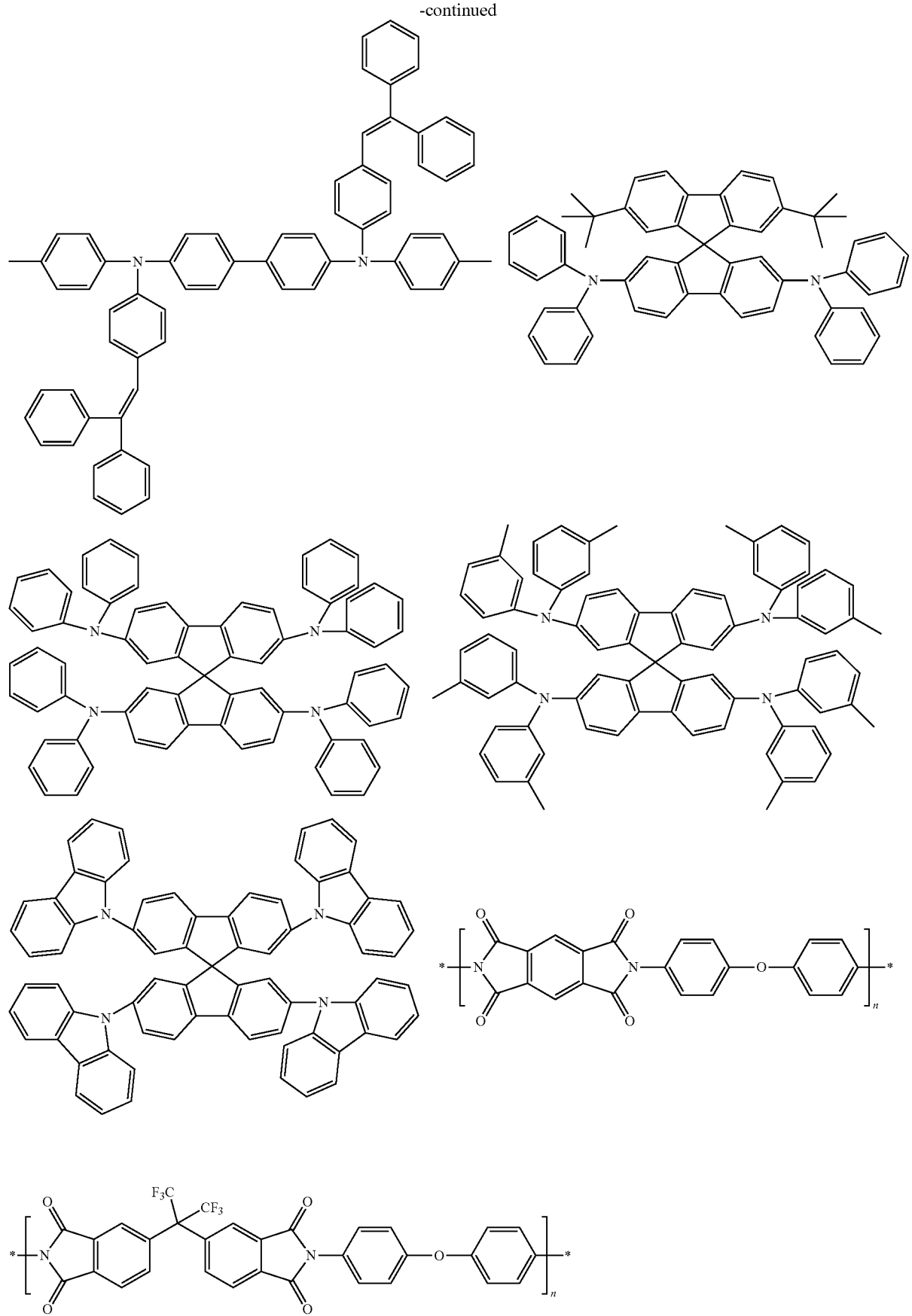

-continued
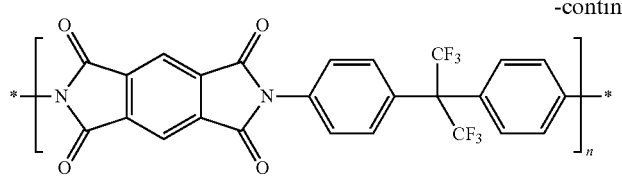
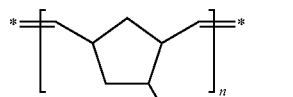
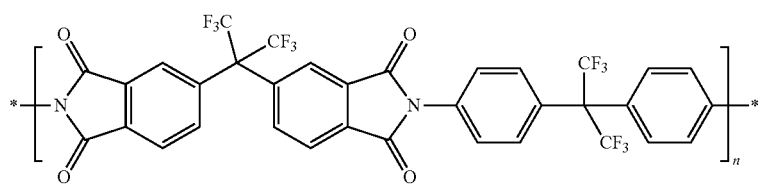
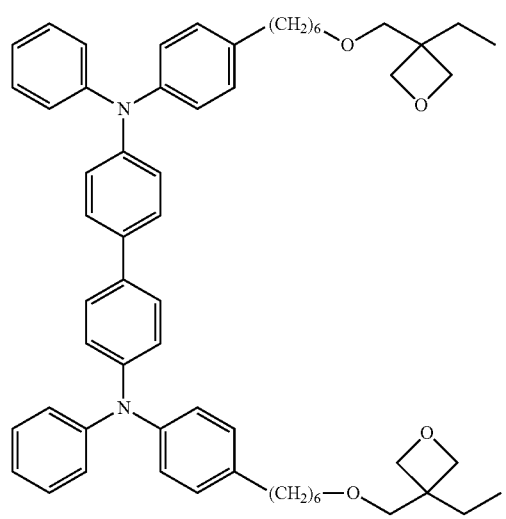
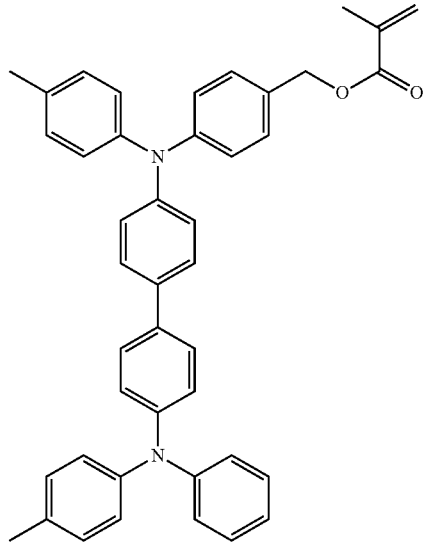
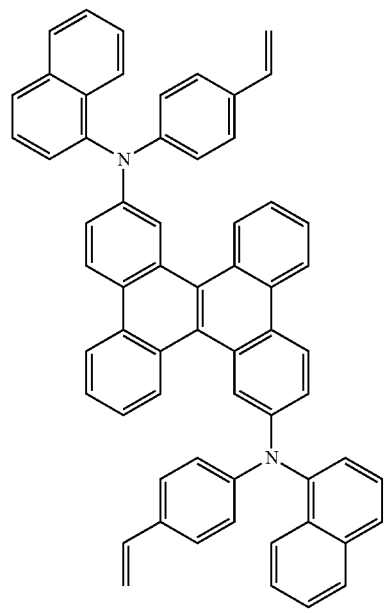

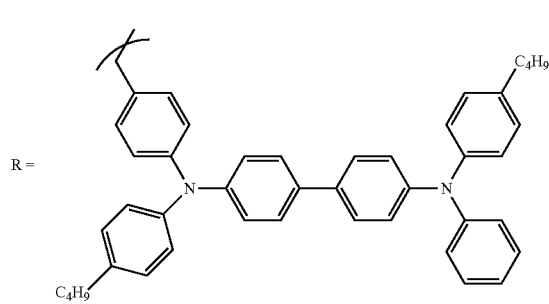
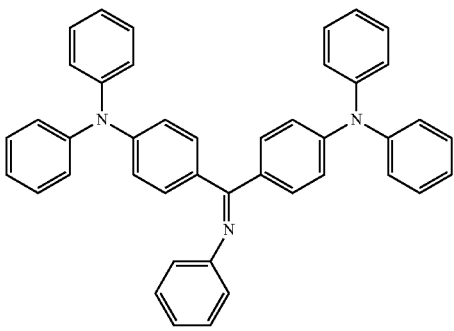
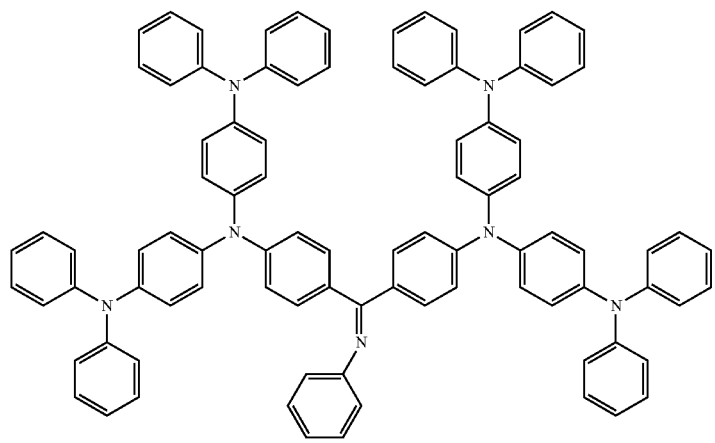
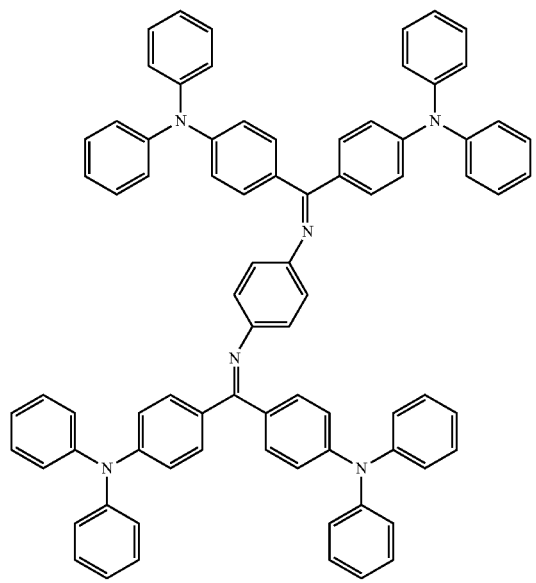

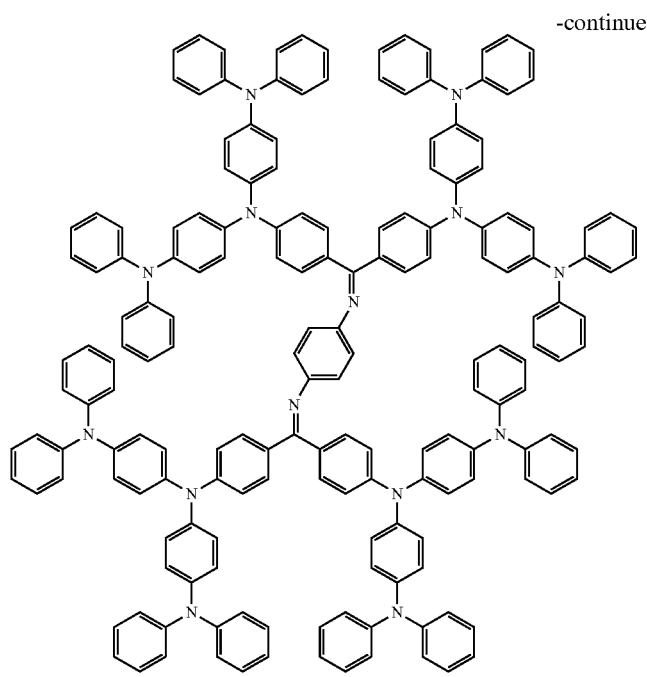
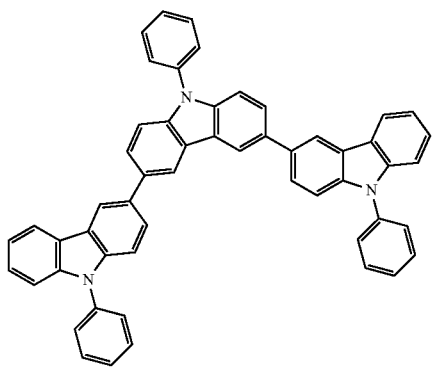
Preferred examples of a compound that may be used as the electron barrier material are shown below.
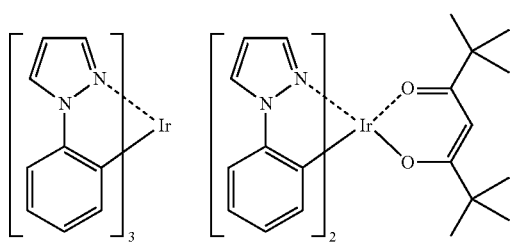
-continued
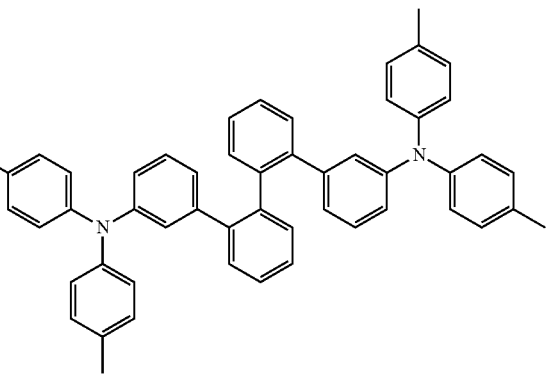
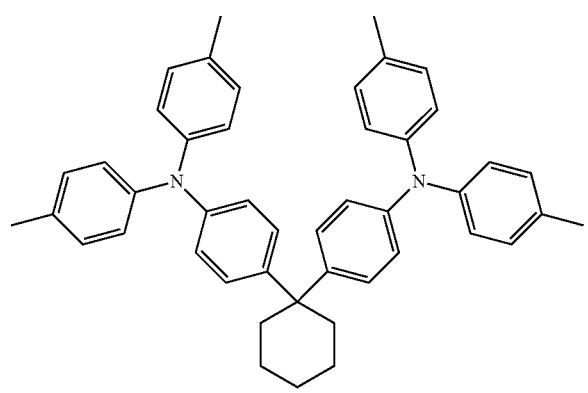
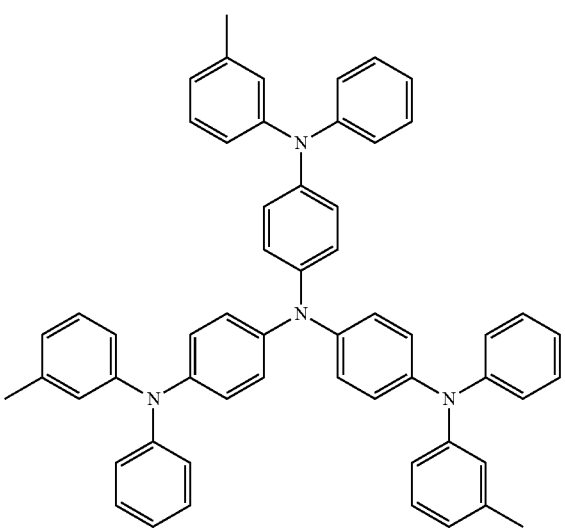

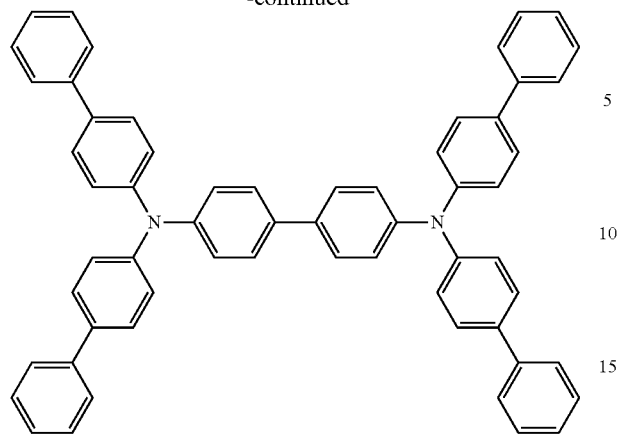
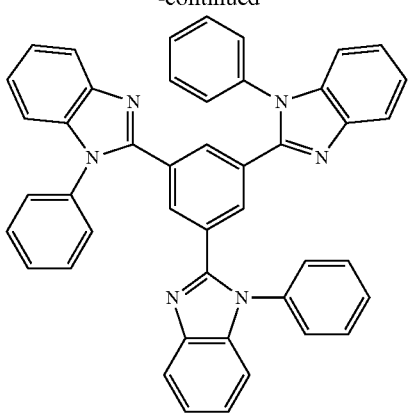
Preferred examples of a compound that may be used as the hole barrier material are shown below.
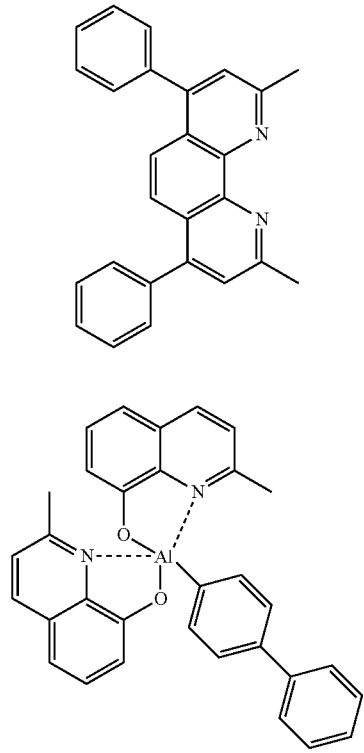
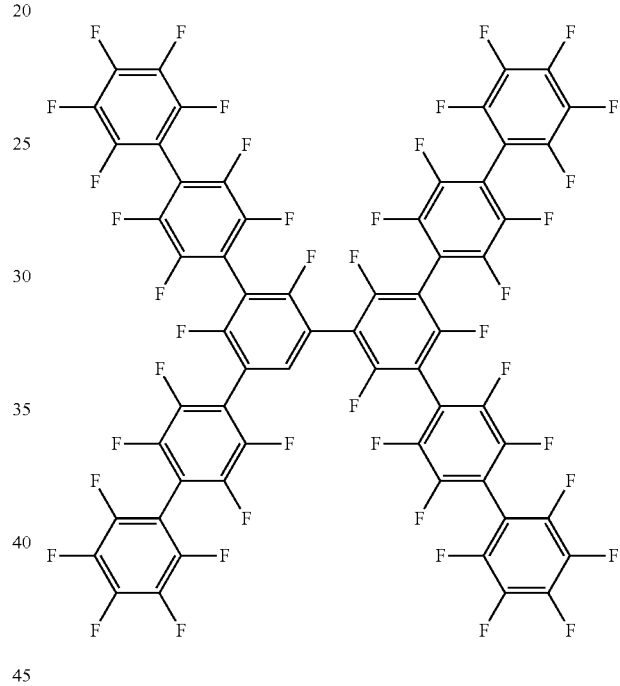
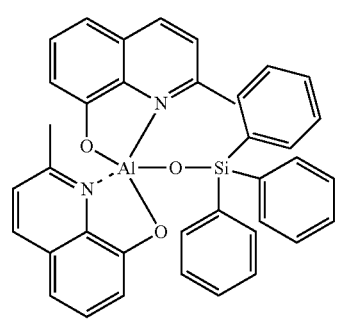
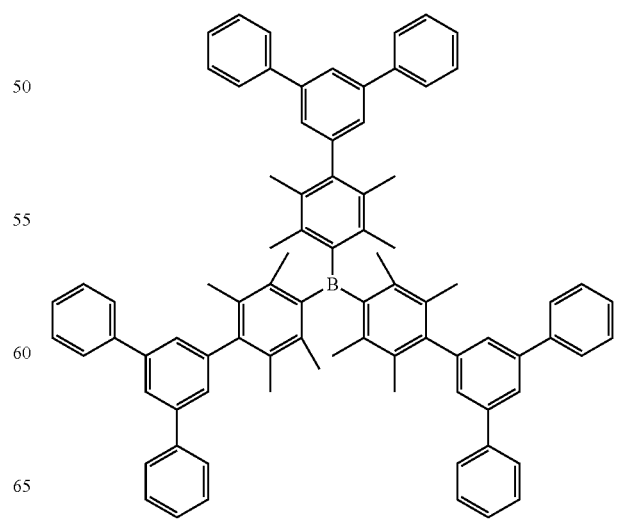

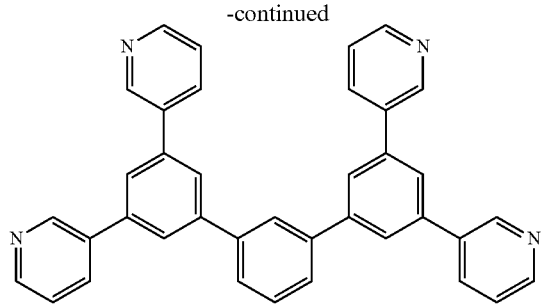
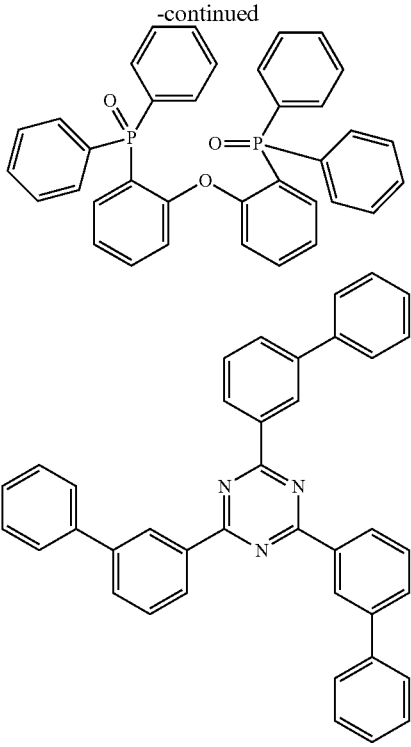
Preferred examples of a compound that may be used as the electron transporting material are shown below.
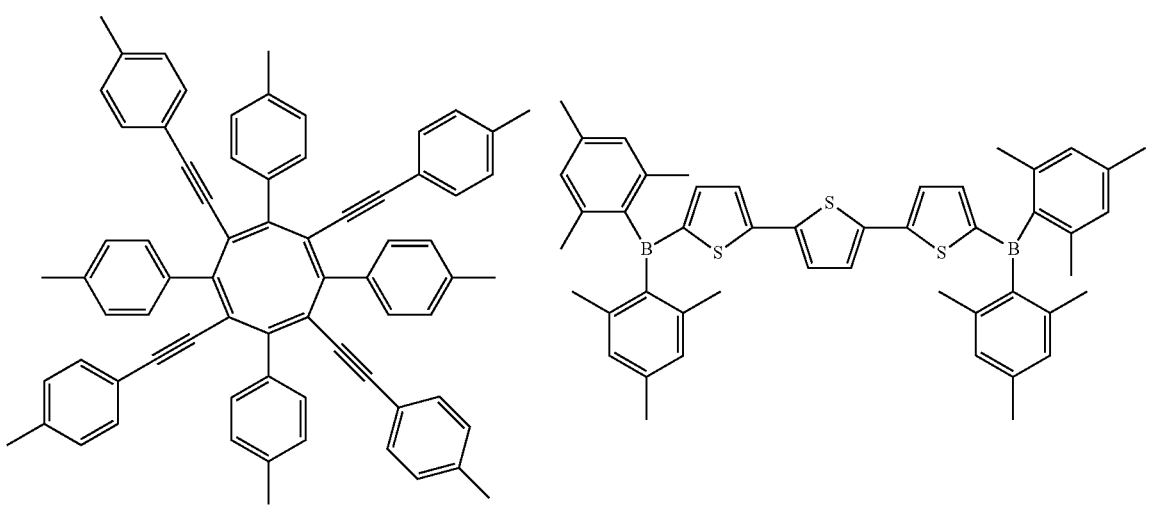
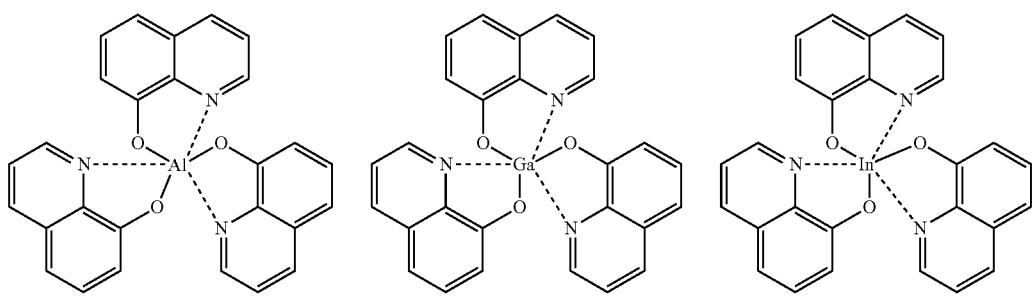

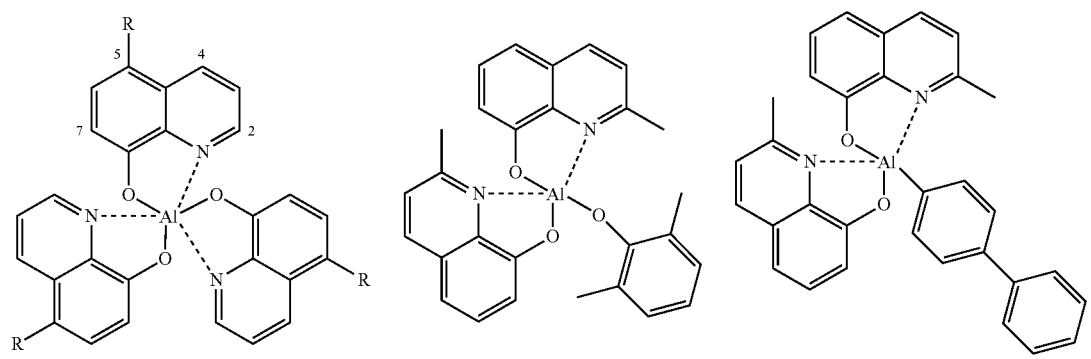
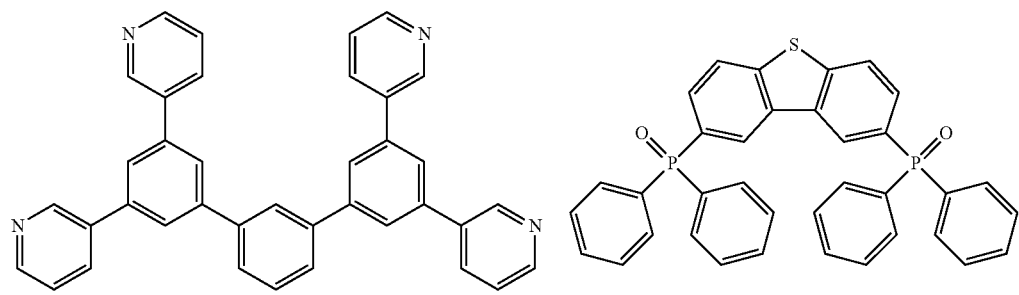
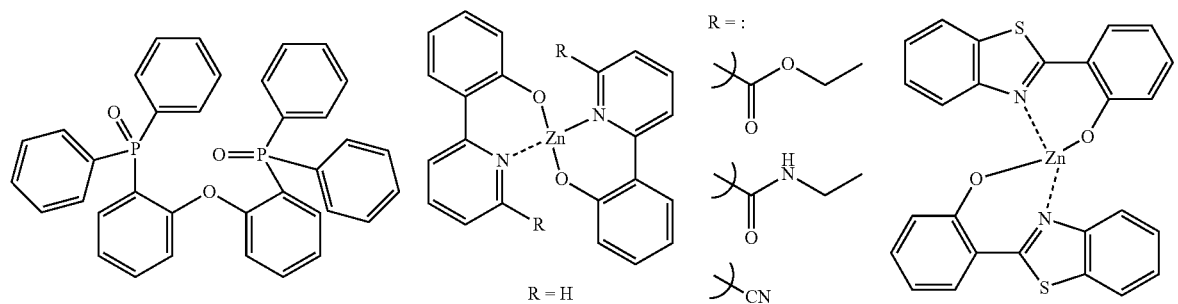
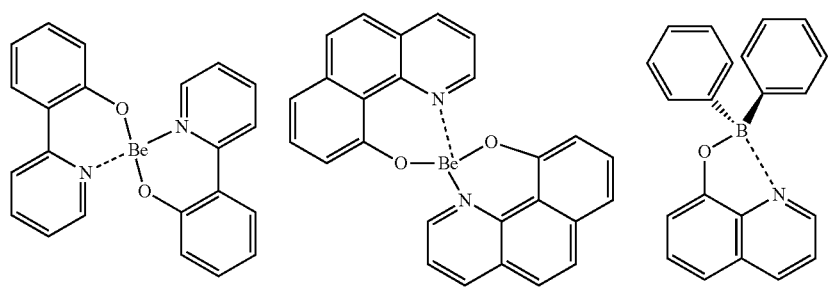

-continued
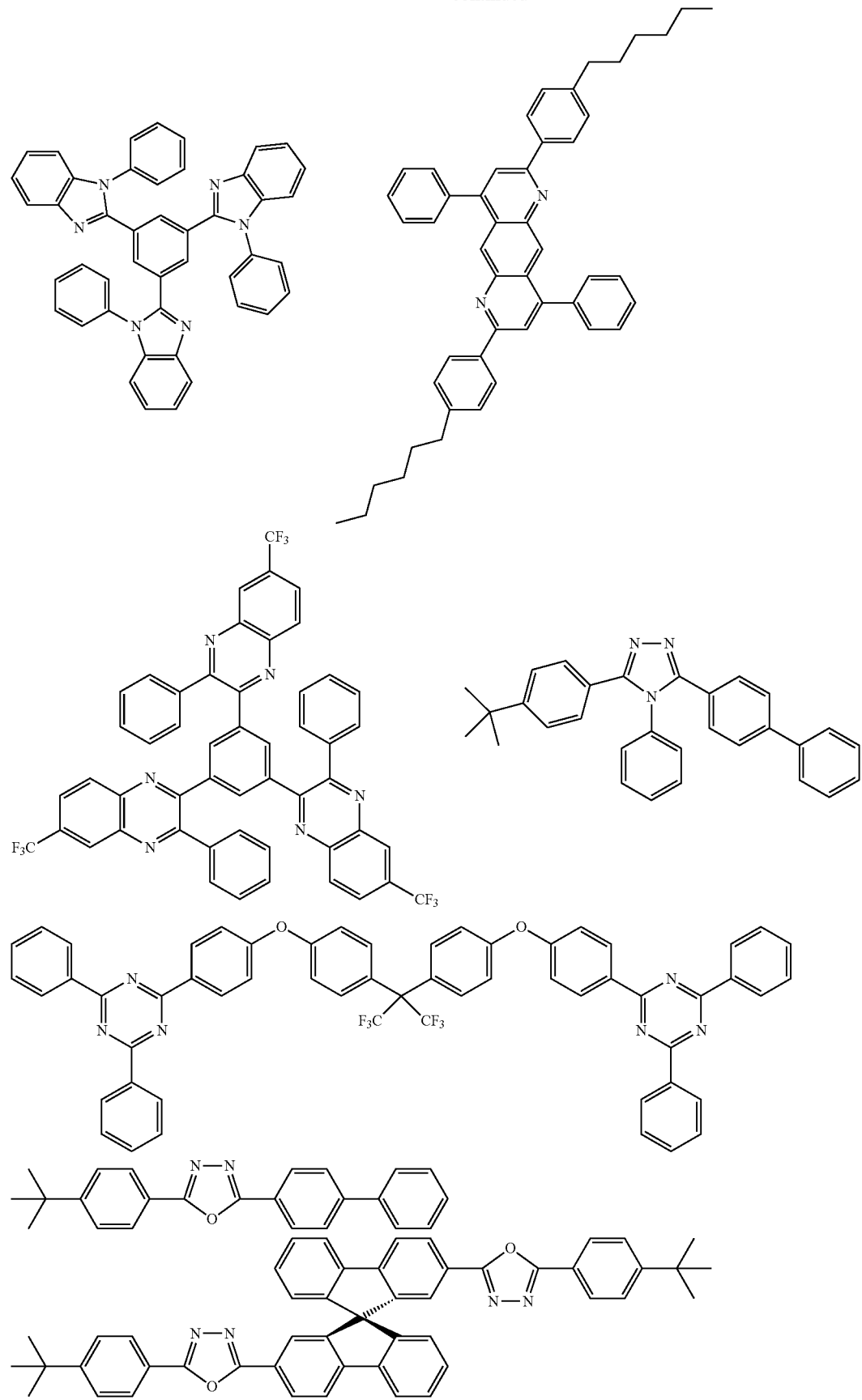

-continued
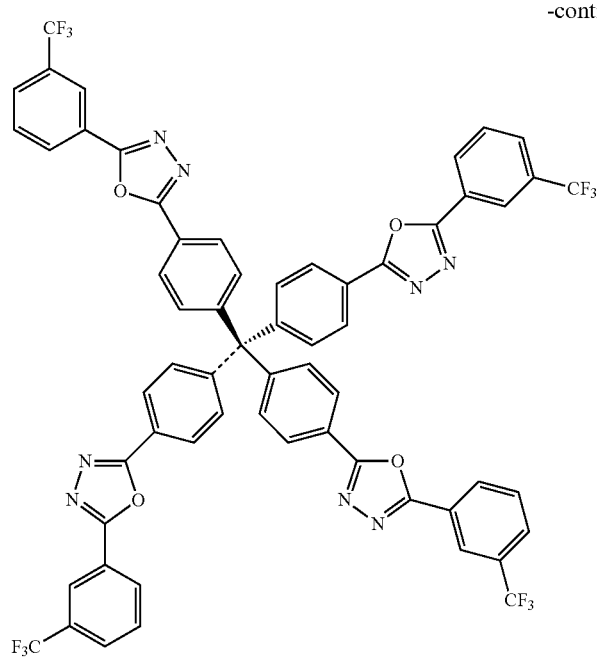
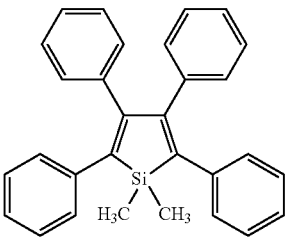
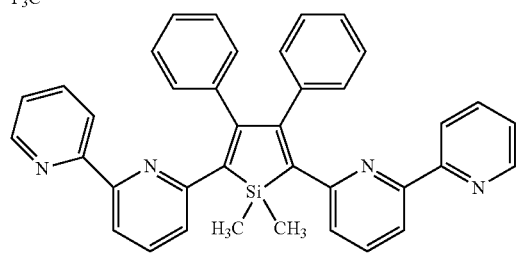
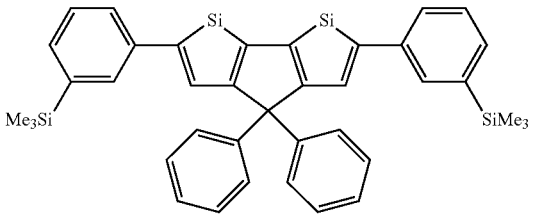
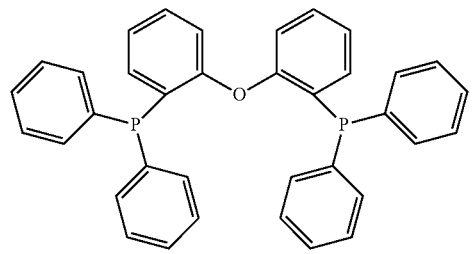
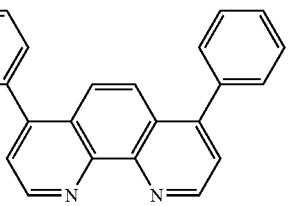
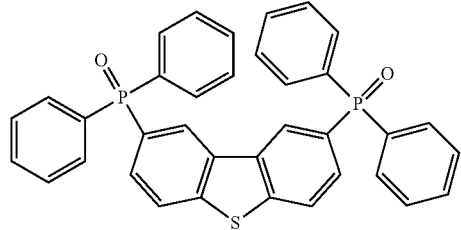
Preferred examples of a compound that may be used as the electron injection material are shown below.
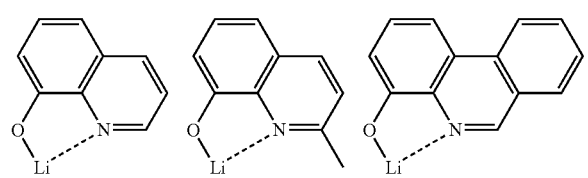
-continued
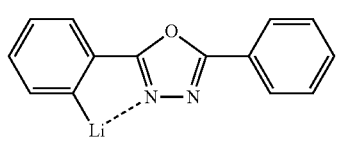
Preferred examples of a compound as a material that may be added are shown below. For example, the compound may be added as a stabilizing material.

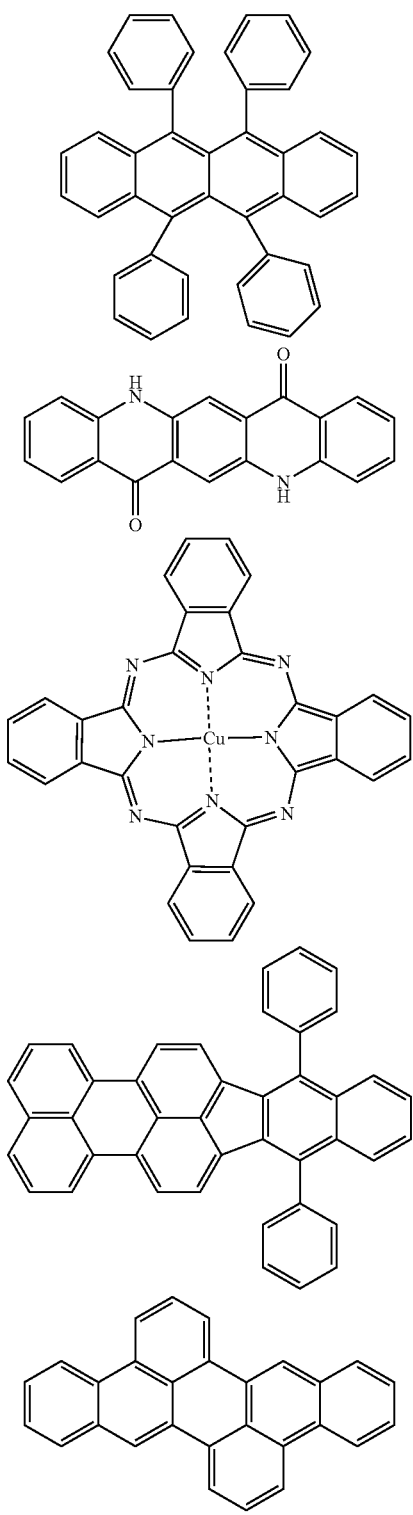

The organic electroluminescent device thus produced by the aforementioned method emits light on application of an electric field between the anode and the cathode of the device. In this case, when the light emission is caused by the excited singlet energy, light having a wavelength that corresponds to the energy level thereof may be confirmed as fluorescent light and delayed fluorescent light. When the light emission is caused by the excited triplet energy, light having a wavelength that corresponds to the energy level thereof may be confirmed as phosphorescent light. The normal fluorescent light has a shorter fluorescent light lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light emitting device that is largely improved in light emission efficiency may be obtained by adding the compound represented by the general formula (1) in the light emitting layer. The organic light emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below.

Synthesis Example 1

Synthesis of Compound 1

4-Bromoacetophenone (11.2 g, 56.3 mmol), benzaldehyde (2.87 mL, 28.1 mmol), and ammonium acetate (27.8 g, 0.366 mmol) were mixed in acetic acid (60 mL), and refluxed for 5 hours. After cooling to room temperature, a solid content obtained by filtration was rinsed with acetic acid, and after drying, recrystallized from ethyl acetate, thereby providing 2,6-bis(4-bromophenyl)-4-phenylpyridine as a colorless solid matter (2.9 g, yield: 22%).

$^1$H NMR (CDCl$_3$, 400 MHz): δ 7.47-7.57 (m, 3H), 7.62-7.66 (m, 4H), 7.71-7.75 (m, 2H), 7.87 (s, 2H), 8.04-8.09 (m, 4H)

$^{13}$C NMR (CDCl$_3$, 100 MHz): δ 117.15, 123.65, 127.16, 128.65, 129.19, 131.88, 136.40, 138.21, 138.66, 150.63, 156.44

2,6-Bis(4-bromophenyl)-4-phenylpyridine (1.03 g, 2.24 mmol), 10H-phenoxazine (1.02 g, 5.57 mmol), and potassium carbonate (1.57 g, 11.2 mmol) were mixed in toluene (50 mL), and after bubbling with nitrogen for 15 minutes, palladium acetate (15 mg, 0.07 mmol) and tri-tert-butyl phosphate (10% by weight hexane solution, 0.56 mL, 0.27 mmol) were added thereto, followed by refluxing for 48 hours. The product was cooled to room temperature, filtered with silica gel, and rinsed with ethyl acetate/methylene chloride/toluene (1/5/5). The filtrate was concentrated to provide a solid matter, which was purified by silica gel column chromatography with ethyl acetate/toluene/petrol (2.5/20/77.5), then methylene chloride/petrol (35/65), and then methylene chloride/toluene (60/40), thereby providing the compound 1 as a pale yellow solid matter (1.34 g, yield: 89%). The compound was further purified by recrystallization from toluene and sublimation purification (320° C., $10^{-6}$ mBar).

m.p.: 325-331° C. (DSC)

$^1$H NMR (CDCl$_3$, 400 MHz): δ 6.05 (d, J=7.7 Hz, 4H), 6.58-6.74 (m, 12H), 7.50-7.61 (m, 7H), 7.79-7.84 (m, 2H), 8.02 (s, 2H), 8.44 (d, J=8.3 Hz, 4H)

$^{13}$C NMR (CDCl$_3$, 100 MHz): δ 113.33, 115.49, 117.79, 121.42, 123.26, 127.20, 129.28, 129.37, 129.91, 131.21, 134.23, 138.54, 139.46, 139.88, 143.97, 150.84, 156.80

HRMS (EI) m/z: 670.2483 C$_{47}$H$_{32}$O$_2$N$_3$ [M+H]$^+$ requires 670.2489

Synthesis Example 2

Synthesis of Compound 2

2,6-Bis(4-bromophenyl)-4-phenylpyridine (2.87 g, 6.21 mmol), 10H-phenothiazine (3.03 g, 15.5 mmol), and potassium carbonate (4.35 g, 31.1 mmol) were mixed in toluene (70 mL), and after bubbling with nitrogen for 15 minutes, palladium acetate (84 mg, 0.37 mmol) and tri-tert-butyl phosphate (10% by weight toluene solution, 3.60 mL, 1.49 mmol) were added thereto, followed by refluxing for 48 hours. The product was cooled to room temperature, filtered with silica gel, and rinsed with ethyl acetate/methylene chloride/toluene (1/5/5). The filtrate was concentrated to provide a solid matter, which was purified by silica gel column chromatography with ethyl acetate/toluene/petrol (2.5/20/77.5), and then methylene chloride/petrol (30/70), thereby providing the compound 2 as a pale yellow solid matter (4.13 g, yield: 95%). The compound was further purified by recrystallization from toluene and sublimation purification (315° C., $10^{-6}$ mBar).

m.p.: 254-260° C. (DSC)

$^1$H NMR (C$_6$D$_6$, 400 MHz): δ 6.41 (dd, J=1.2, 8.1 Hz, 4H), 6.64 (dt, J=1.3, 7.4 Hz, 4H), 6.68-6.74 (m, 4H), 7.01 (dd, J=1.6, 7.5 Hz, 4H), 7.20-7.30 (m, 7H), 7.46-7.50 (m, 2H), 7.69 (s, 2H), 8.19-8.22 (m, 4H)

$^{13}$C NMR (C$_6$D$_6$, 100 MHz): δ 121.46, 123.13, 127.13, 127.30, 127.53, 127.88, 128.12, 129.29, 129.86, 130.84, 139.15, 139.31, 142.48, 144.70, 150.73, 157.21

HRMS (EI) m/z: 701.1949 C$_{47}$H$_{32}$N$_3$S$_2$ [M]$^+$ requires 701.1954

Synthesis Example 3

Synthesis of Compound 5

2,6-Bis(4-bromophenyl)-4-phenylpyridine (1.0 g, 2.16 mmol), 9,9-dimethyl-9,10-dihydroacridine (1.04 g, 4.98 mmol), and sodium tert-butoxide (520 mg, 5.4 mmol) were mixed in toluene (40 mL), and after bubbling with nitrogen for 15 minutes, tris(dibenzylideneacetone) dipalladium(0) (20 mg, 0.022 mmol) and 1,1'-bis(diphenylphosphino) ferrocene (24 mg, 0.044 mmol) were added thereto, followed by refluxing for 72 hours. The product was cooled to room temperature, filtered with silica gel, and rinsed with ethyl acetate/methylene chloride/toluene (1/5/5). The filtrate was concentrated to provide a solid matter, which was purified by silica gel column chromatography with toluene/petrol/methylene chloride (25/75/0), then (30/60/10), and then (30/50/20), thereby providing the compound 5 as a colorless solid matter (1.45 g, yield: 93%). The compound was further purified by recrystallization from toluene/petrol and sublimation purification (320° C., $10^{-6}$ mBar).

m.p.: 338-343° C. (DSC)

$^1$H NMR (CDCl$_3$, 400 MHz): δ 1.74 (s, 12H), 6.42 (dd, J=1.3, 8.0 Hz, 4H), 6.94-7.04 (m, 8H), 7.48-7.63 (m, 11H), 7.83-7.88 (m, 2H), 8.08 (s, 2H), 8.49-8.53 (m, 4H)

$^{13}$C NMR (CDCl$_3$, 100 MHz): δ 31.33, 35.99, 114.12, 117.70, 120.62, 125.28, 126.38, 127.21, 129.24, 129.71, 130.01, 131.71, 138.69, 139.37, 140.79, 142.14, 150.68, 157.02

HRMS (APCI) m/z: 721.3452 C$_{53}$H$_{43}$N$_3$[M]$^+$ requires 721.3451

Synthesis Example 4

Synthesis of Compound 19

Acetophenone (9.71 mL, 83.2 mmol), 4-bromobenzaldehyde (7.7 g, 41.8 mmol), and ammonium acetate (41 g, 0.54 mmol) were mixed in acetic acid (80 mL), and refluxed for 24 hours. After cooling to room temperature, a solid content obtained by filtration was rinsed with acetic acid, and the component that was insoluble in ethyl acetate was taken out, rinsed with a saturated sodium hydrogen carbonate aqueous solution and a saturated sodium chloride aqueous solution, and dried. Thereafter, the product was subjected to silica gel chromatograph with ethyl acetate/petrol (2/98) and recrystallized from ethanol, thereby providing 4-(4-bromophenyl)-2,6-diphenylpyridine as a colorless solid matter (3.0 g, yield: 19%).

$^1$H NMR (CDCl$_3$, 400 MHz): δ 7.43-7.56 (m, 6H), 7.59-7.69 (m, 4H), 7.85 (s, 2H), 8.12-8.22 (m, 4H)

$^{13}$C NMR (CDCl$_3$, 100 MHz): δ 116.74, 123.39, 127.11, 128.73, 129.16, 131.82, 132.28, 137.95, 139.37, 148.96, 157.69

4-(4-Bromophenyl)-2,6-diphenylpyridine (2.18 g, 5.67 mmol), 10H-phenoxazine (1.19 g, 6.52 mmol), and potassium carbonate (1.59 g, 11.3 mmol) were mixed in toluene (50 mL), and after bubbling with nitrogen for 15 minutes, palladium acetate (76 mg, 0.34 mmol) and tri-tert-butyl phosphate (10% by weight hexane solution, 2.83 mL, 1.36 mmol) were added thereto, followed by refluxing for 48 hours. The product was cooled to room temperature, filtered with silica gel, and rinsed with ethyl acetate/methylene chloride/toluene (1/5/5). The filtrate was concentrated to provide a solid matter, which was purified by silica gel column chromatography with ethyl acetate/toluene/petrol (2.5/5/92.5), thereby providing the compound 19 as a pale yellow solid matter (2.6 g, yield: 94%). The compound was further purified by recrystallization from methylene chloride/ethyl acetate and sublimation purification (245° C., $10^{-6}$ mBar).

m.p.: 235-242° C. (DSC)

$^1$H NMR (CDCl$_3$, 400 MHz): δ 6.03 (dd, J=1.6, 7.8 Hz, 2H), 6.63 (dt, J=1.8, 7.3 Hz, 2H), 6.68 (dt, J=1.4, 7.3 Hz, 2H), 6.73 (dd, J=1.8, 7.8 Hz, 2H), 7.44-7.57 (m, 8H), 7.96 (s, 2H), 7.96-8.00 (m, 2H), 8.22-8.27 (m, 4H)

$^{13}$C NMR (CDCl$_3$, 100 MHz): δ113.25, 115.57, 117.01, 121.54, 123.28, 127.13, 128.76, 129.20, 129.88, 131.61, 134.16, 139.25, 139.37, 139.76, 143.96, 149.12, 157.69

HRMS (EI) m/z: 488.1884 $C_{35}H_{24}N_2O$ [M]$^+$ requires 488.1884

Synthesis Example 5

Synthesis of Compound 20

4-(4-Bromophenyl)-2,6-diphenylpyridine (750 mg, 1.95 mmol), 9,9-dimethyl-9,10-dihydroacridine (410 g, 1.95 mmol), and sodium tert-butoxide (280 mg, 2.92 mmol) were mixed in toluene (40 mL), and after bubbling with nitrogen for 15 minutes, tris(dibenzylideneacetone) dipalladium(0) (36 mg, 0.04 mmol) and 1,1'-bis(diphenylphosphino) ferrocene (43 mg, 0.08 mmol) were added thereto, followed by refluxing for 48 hours. The product was cooled to room temperature, filtered with silica gel, and rinsed with ethyl acetate/toluene (5/95). The filtrate was concentrated to provide a solid matter, which was purified by silica gel column chromatography with toluene/petrol (27/73), thereby providing the compound 20 as a colorless solid matter (795 mg, yield: 79%). The compound was further purified by recrystallization from toluene/petrol and sublimation purification (230° C., 10$^{-6}$ mBar).

m.p.: 200-205° C. (DSC)

$^1$H NMR (CDCl$_3$, 400 MHz): δ 1.57 (s, 6H), 6.37 (dd, J=1.3, 8.0 Hz, 2H), 6.94-7.05 (m, 4H), 7.45-7.58 (m, 10H), 8.01 (s, 2H), 8.01-8.04 (m, 2H), 8.25-8.29 (m, 4H)

$^{13}$C NMR (CDCl$_3$, 100 MHz): δ31.30, 36.00, 114.01, 117.07, 120.74, 125.34, 126.41, 127.14, 128.75, 129.17, 129.69, 130.10, 132.09, 138.95, 139.42, 140.74, 142.06, 149.29, 157.67

HRMS (APCI) m/z: 514.2408 $C_{38}H_{30}N_2$[M]$^+$ requires 514.2404

Synthesis Example 6

Synthesis of Compound 21

4-(4-Bromophenyl)-2,6-diphenylpyridine (720 mg, 1.87 mmol), 9,9-diphenyl-9,10-dihydroacridine (620 g, 1.87 mmol), and sodium tert-butoxide (210 mg, 2.2 mmol) were mixed in toluene (40 mL), and after bubbling with nitrogen for 15 minutes, tris(dibenzylideneacetone) dipalladium(0) (18 mg, 0.02 mmol) and 1,1'-bis(diphenylphosphino) ferrocene (22 mg, 0.04 mmol) were added thereto, followed by refluxing for 48 hours. The product was cooled to room temperature, filtered with silica gel, and rinsed with ethyl acetate/toluene (5/95). The filtrate was concentrated to provide a solid matter, which was purified by silica gel column chromatography with methylene chloride/petrol (15/85), then (20/80), and then (30/70), thereby providing the compound 21 as a colorless solid matter (1.45 g, yield: 93%). The compound was further purified by recrystallization from toluene/petrol and sublimation purification (285° C., 10$^{-6}$ mBar).

m.p.: 288-293° C. DSC)

$^1$H NMR (CDCl$_3$, 400 MHz): δ 6.52 (dd, J=0.7, 8.6 Hz, 2H), 6.89-6.96 (m, 4H), 7.01-7.06 (m, 4H), 7.10 (ddd, J=2.4, 6.4, 8.4 Hz, 2H), 7.23-7.32 (m, 8H), 7.45-7.50 (m, 2H), 7.51-7.57 (m, 4H), 7.89-7.94 (m, 2H), 7.96 (s, 2H), 8.22-8.26 (m, 4H)

$^{13}$C NMR (CDCl$_3$, 100 MHz): δ 56.76, 114.03, 117.05, 120.34, 126.30, 126.90, 127.12, 127.64, 128.75, 129.16, 129.32, 129.73, 130.10, 130.39, 132.02, 138.93, 139.41, 141.60, 142.04, 146.38, 149.28, 157.65

HRMS (APCI) m/z: 638.2716 $C_{48}H_{34}N_2$[M]$^+$ requires 638.2717

Synthesis Example 7

Synthesis of Compound 22

2,6-Bis(4-bromophenyl)-4-phenylpyridine (340 mg, 0.74 mmol), 9,9-diphenyl-9,10-dihydroacridine (540 mg, 1.62 mmol), and sodium tert-butoxide (200 mg, 2.06 mmol) were mixed in toluene (40 mL), and after bubbling with nitrogen for 15 minutes, tris(dibenzylideneacetone) dipalladium(0) (27 mg, 0.03 mmol) and 1,1'-bis(diphenylphosphino) ferrocene (33 mg, 0.06 mmol) were added thereto, followed by refluxing for 24 hours. The product was cooled to room temperature, filtered with silica gel, and rinsed with ethyl acetate/toluene (5/95). The filtrate was concentrated to provide a solid matter, which was purified by silica gel column chromatography with toluene/petrol/methylene chloride (25/75/0), and then (30/40/30), thereby providing the compound 22 as a colorless solid matter (610 mg, yield: 86%). The compound was further purified by recrystallization from toluene/methylene chloride and sublimation purification (380° C., 10$^{-6}$ mBar).

$^1$H NMR (CDCl$_3$, 400 MHz): δ 6.54 (dd, J=0.9, 8.4 Hz, 4H), 6.86-6.94 (m, 8H), 7.01-7.09 (m, 12H), 7.21-7.30 (m, 16H), 7.47-7.58 (m, 3H), 7.76-7.81 (m, 2H), 7.98 (s, 2H), 8.34-8.39 (m, 4H)

$^{13}$C NMR (CDCl$_3$, 100 MHz): δ 56.75, 114.1, 117.59, 120.21, 126.25, 126.86, 127.17, 127.62, 129.22, 129.30, 129.54, 130.04, 130.40, 131.62, 138.68, 139.32, 141.67, 142.08, 146.45, 150.62, 156.91

HRMS (APCI) m/z: 969.4073 $C_{73}H_{51}N_3$[M]$^+$ requires 969.4078

Synthesis Example 8

Synthesis of Compound 23

2,6-Bis(4-bromophenyl)-4-phenylpyridine (480 mg, 1.04 mmol), 9,9-bis(5-methylthiophen-2-yl)-9,10-dihydroacridine (850 g, 2.28 mmol), and sodium tert-butoxide (280 mg, 2.91 mmol) were mixed in toluene (40 mL), and after bubbling with nitrogen for 15 minutes, tris(dibenzylideneacetone) dipalladium(0) (38 mg, 0.04 mmol) and 1,1'-bis(diphenylphosphino) ferrocene (46 mg, 0.08 mmol) were added thereto, followed by refluxing for 8 hours. The product was cooled to room temperature, filtered with silica gel, and rinsed with ethyl acetate/petrol (10/90). The filtrate was concentrated to provide a solid matter, which was purified by silica gel column chromatography with toluene/petrol (20/80), then (30/70), and then (40/60), thereby providing the compound 23 as a pale yellow solid matter (840 mg, yield: 74%). The compound was further recrystallized from toluene/methylene chloride/petrol.

$^1$H NMR (CDCl$_3$, 400 MHz): δ 2.43 (2, 12H), 6.46-6.50 (m, 8H), 6.56-6.60 (m, 4H), 6.93 (dt, J=1.2, 7.7 Hz, 4H), 7.08 (ddd, J=1.6, 8.3, 8.5 Hz, 4H), 7.27 (dd, J=1.5, 7.8 Hz, 4H), 7.38-7.42 (m, 4H), 7.49-7.61 (m, 3H), 7.80-7.84 (m, 2H), 8.03 (s, 2H), 8.41-8.45 (m, 4H)

$^{13}$C NMR (CDCl$_3$, 100 MHz): δ 15.46, 50.75, 114.15, 117.68, 120.23, 123.94, 127.19, 127.55, 127.65, 128.50, 129.23, 129.28, 129.49, 131.72, 138.68, 139.45, 140.07, 140.75, 141.70, 150.53, 150.67, 156.95

HRMS (APCI) m/z: 1050.3040 $C_{73}H_{51}N_3$[M+H]$^+$ requires 1050.3039

Example 1

Production and Evaluation of Solution of Compound 1 (Solution)

Figure 2:
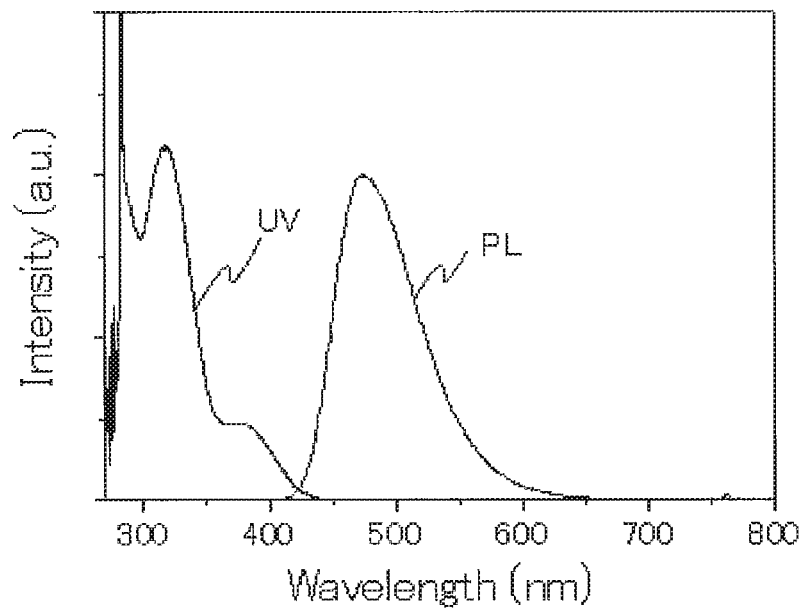
FIG. 2 is the light emission spectrum of the toluene solution of the compound 1 in Example 1.
Figure 3:
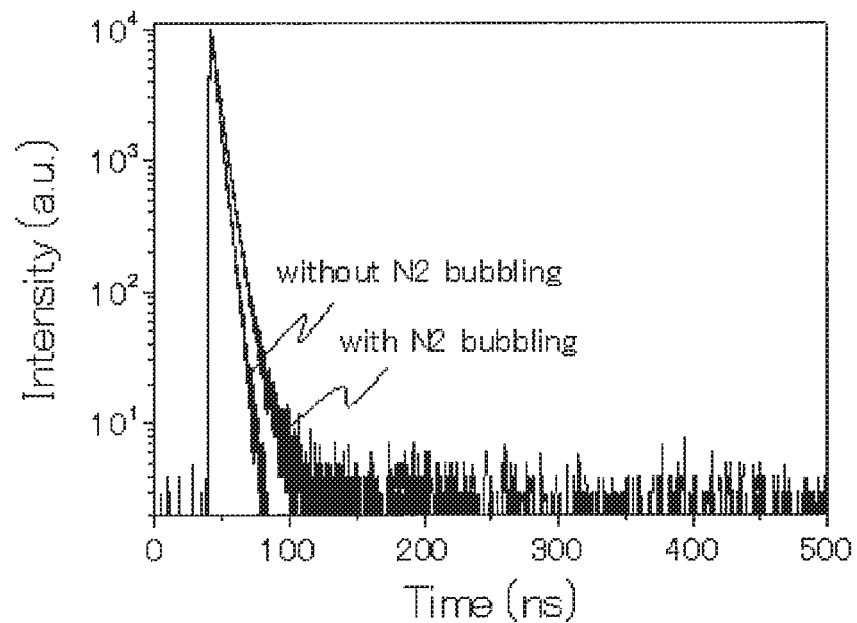
FIG. 3 is the transient decay curves of the toluene solution of the compound 1 in Example 1.

A toluene solution (concentration: $10^{-4}$ mol/L) of the compound 1 synthesized in Synthesis Example 1 was prepared and irradiated with ultraviolet light at 300 K under bubbling with nitrogen, and thus fluorescent light having a peak wavelength of 475 nm was observed as shown in FIG. 2. The measurement with a compact fluorescence lifetime spectrometer (Quantaurus-tau, produced by Hamamatsu Photonics K.K.) was performed before and after bubbling with nitrogen, and the transient decay curves shown in FIG. 3 were obtained. Fluorescent light having an excitation lifetime of 4.56 ns was observed in the toluene solution of the compound 1 before bubbling with nitrogen, and fluorescent light having an excitation lifetime of 5.80 ns and delayed fluorescent light having an excitation lifetime of 17.1 ns were observed in the toluene solution of the compound 1 after bubbling with nitrogen. The photoluminescent quantum efficiency of the compound 1 in the toluene solution was measured with an absolute PL quantum yields measurement system (Quantaurus-QY, produced by Hamamatsu Photonics K.K.) at an excitation wavelength of 330 nm, and was 21.8% before bubbling with nitrogen and 37.5% after bubbling with nitrogen.

Example 2

Production and Evaluation of Solution of Compound 2 (Solution)

Figure 4:
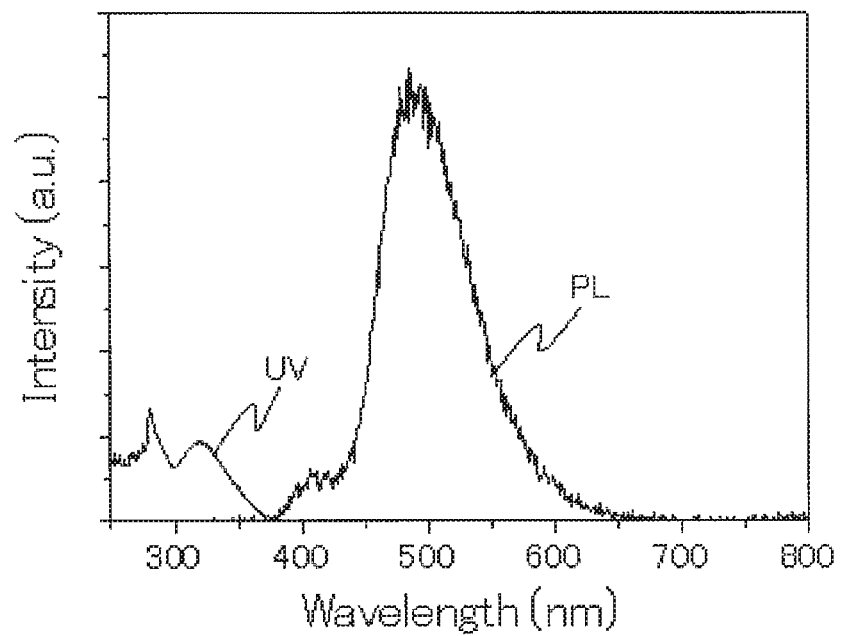
FIG. 4 is the light emission spectrum of the toluene solution of the compound 2 in Example 2.
Figure 5:
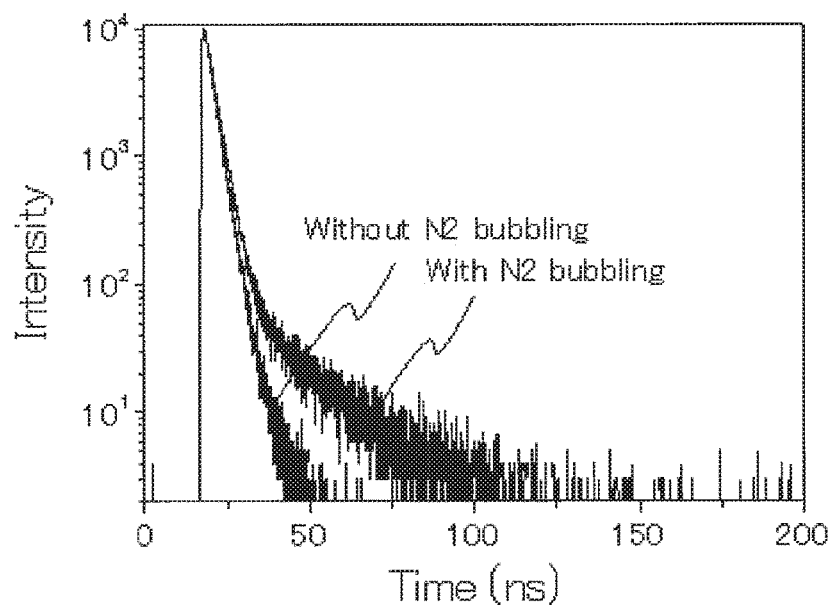
FIG. 5 is the transient decay curves of the toluene solution of the compound 2 in Example 2.

The production and the evaluation of the toluene solution were performed in the same manner as in Example 1 except that the compound 2 synthesized in Synthesis Example 2 was used instead of the compound 1. FIG. 4 shows the light emission spectrum, and FIG. 5 shows the transient decay curves. Fluorescent light having an excitation lifetime of 2.58 ns was observed in the toluene solution of the compound 2 before bubbling with nitrogen, and fluorescent light having an excitation lifetime of 2.85 ns and delayed fluorescent light having an excitation lifetime of 20.6 ns were observed in the toluene solution of the compound 2 after bubbling with nitrogen. The photoluminescent quantum efficiency of the compound was 3.4% before bubbling with nitrogen and 3.8% after bubbling with nitrogen.

Example 3

Production and Evaluation of Solution of Compound 5 (Solution)

Figure 6:
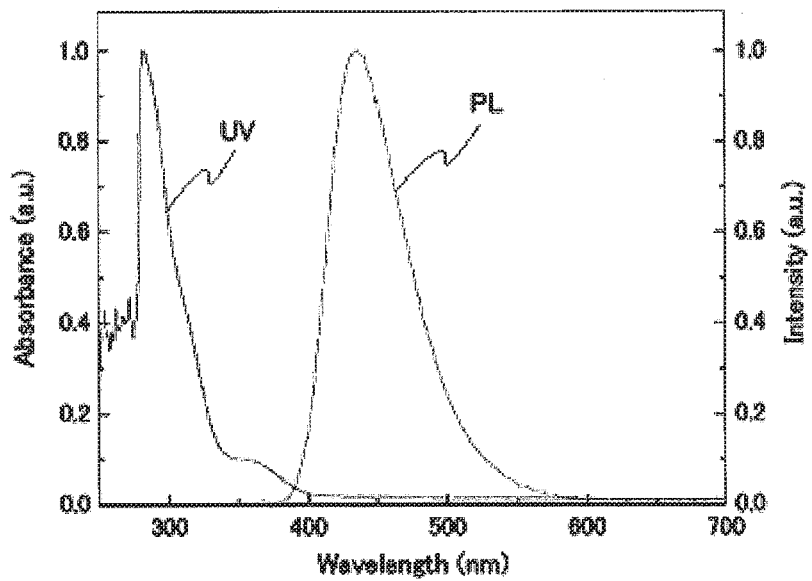
FIG. 6 is the light emission spectrum of the toluene solution of the compound 5 in Example 3.
Figure 7:
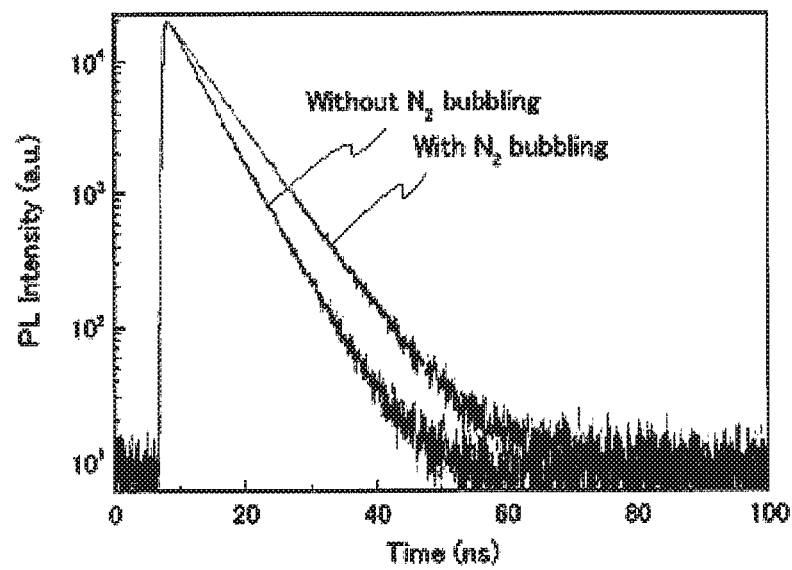
FIG. 7 is the transient decay curves of the toluene solution of the compound 5 in Example 3.

The production and the evaluation of the toluene solution were performed in the same manner as in Example 1 except that the compound 5 synthesized in Synthesis Example 3 was used at a concentration of $10^{-5}$ M instead of the compound 1. FIG. 6 shows the absorption-emission spectra at an excitation wavelength of 354 nm, and FIG. 7 shows the transient decay curves at an excitation wavelength of 340 nm. Light emission with a peak at 435 nm was observed. Fluorescent light having an excitation lifetime of 4.6 ns was observed in the toluene solution of the compound 5 before bubbling with nitrogen, and fluorescent light having an excitation lifetime of 6.1 ns was observed in the toluene solution of the compound 5 after bubbling with nitrogen. The photoluminescent quantum efficiency at an excitation wavelength of 320 nm of the compound was 16.2% before bubbling with nitrogen and 25.7% after bubbling with nitrogen.

Example 4

Production and Evaluation of Solution of Compound 19 (Solution)

Figure 8:
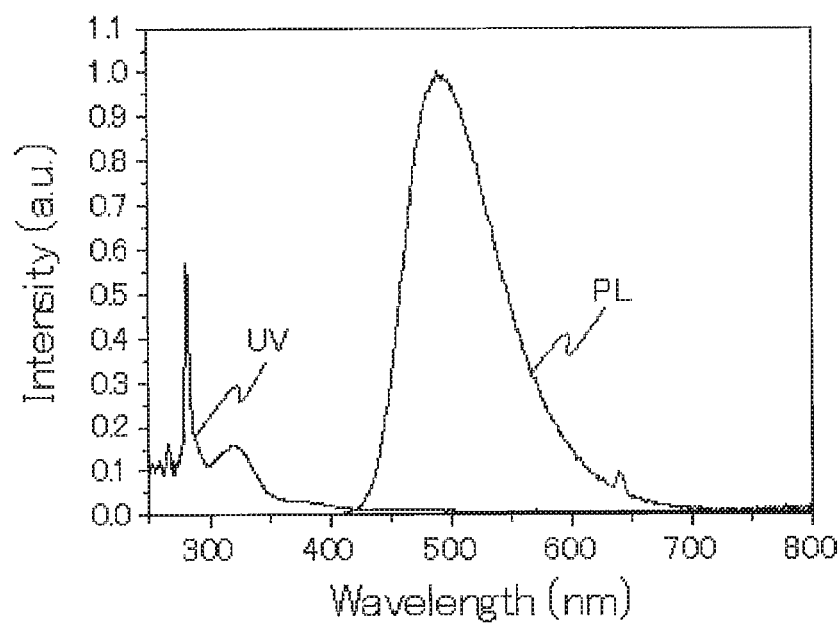
FIG. 8 is the light emission spectrum of the toluene solution of the compound 19 in Example 4.
Figure 9:
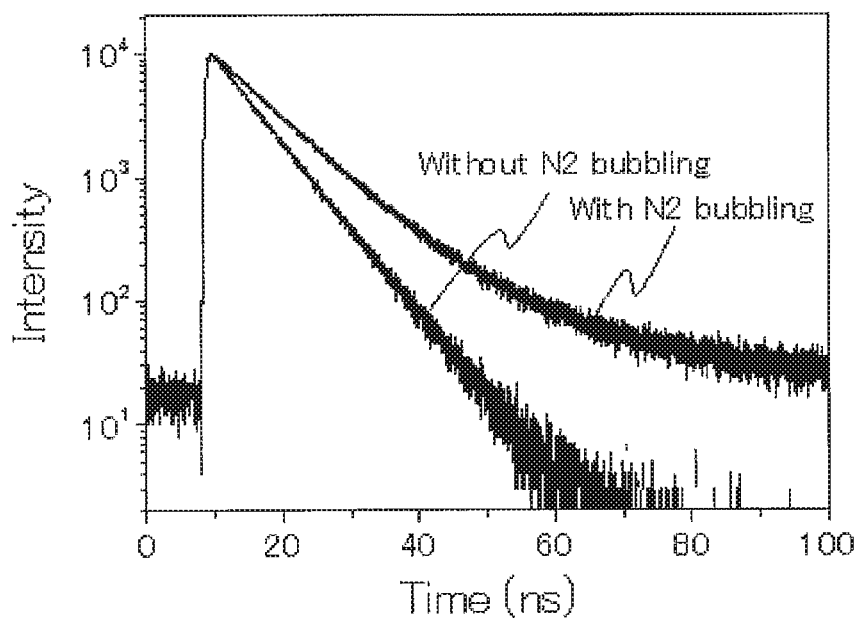
FIG. 9 is the transient decay curves of the toluene solution of the compound 19 in Example 4.

The production and the evaluation of the toluene solution were performed in the same manner as in Example 1 except that the compound 19 synthesized in Synthesis Example 4 was used instead of the compound 1. FIG. 8 shows the light emission spectrum, and FIG. 9 shows the transient decay curves. Fluorescent light having an excitation lifetime of 5.94 ns was observed in the toluene solution of the compound 19 before bubbling with nitrogen, and fluorescent light having an excitation lifetime of 8.39 ns and delayed fluorescent light having an excitation lifetime of 1.56 is were observed in the toluene solution of the compound 19 after bubbling with nitrogen. The photoluminescent quantum efficiency of the compound was 14.8% before bubbling with nitrogen and 24.8% after bubbling with nitrogen.

Example 5

Production and Evaluation of Solution of Compound 20 (Solution)

Figure 10:
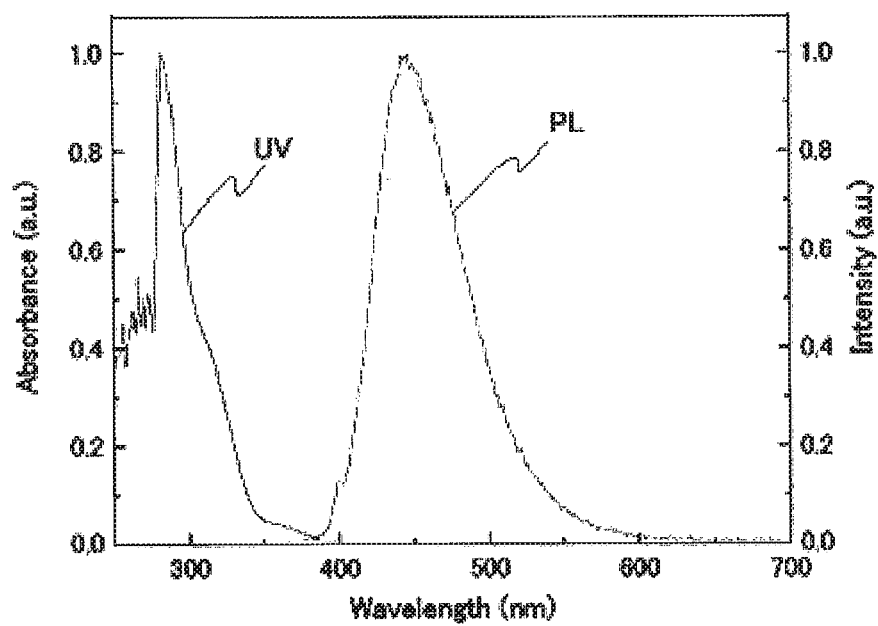
FIG. 10 is the absorption-emission spectra of the toluene solution of the compound 20 in Example 5.
Figure 11:
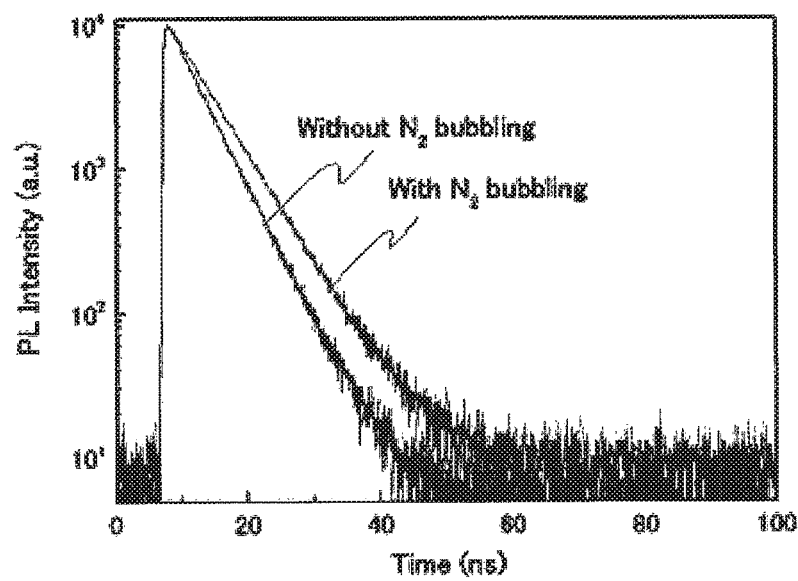
FIG. 11 is the transient decay curves of the toluene solution of the compound 20 in Example 5.

The production and the evaluation of the toluene solution were performed in the same manner as in Example 1 except that the compound 20 synthesized in Synthesis Example 5 was used at a concentration of $10^{-5}$ M instead of the compound 1. FIG. 10 shows the absorption-emission spectra at an excitation wavelength of 356 nm, and FIG. 11 shows the transient decay curves at an excitation wavelength of 340 nm. Light emission with a peak at 445 nm was observed. Fluorescent light having an excitation lifetime of 4.4 ns was observed in the toluene solution of the compound 20 before bubbling with nitrogen, and fluorescent light having an excitation lifetime of 5.6 ns was observed in the toluene solution of the compound 20 after bubbling with nitrogen. The photoluminescent quantum efficiency at an excitation wavelength of 320 nm of the compound was 12.1% before bubbling with nitrogen and 20.3% after bubbling with nitrogen.

Example 6

Production and Evaluation of Solution of Compound 21 (Solution)

Figure 12:
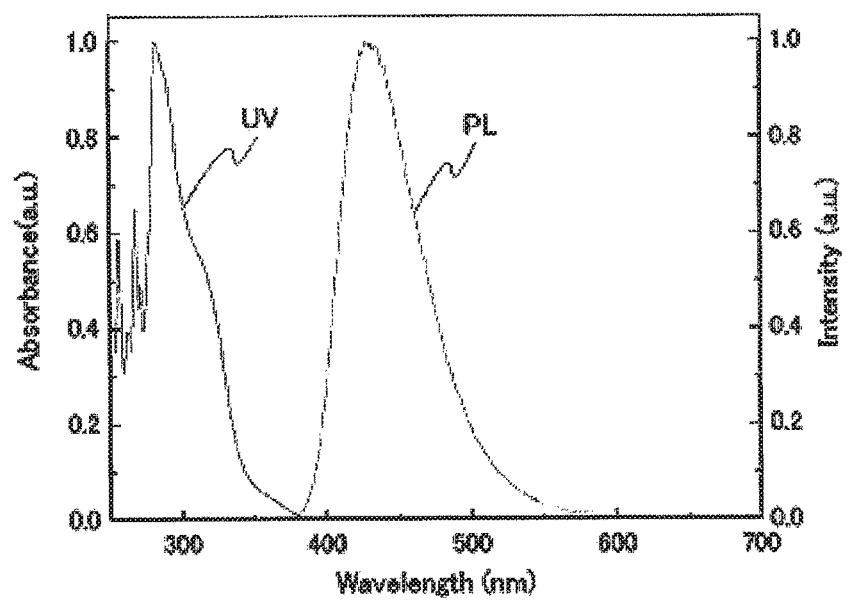
FIG. 12 is the absorption-emission spectra of the toluene solution of the compound 21 in Example 6.
Figure 13:
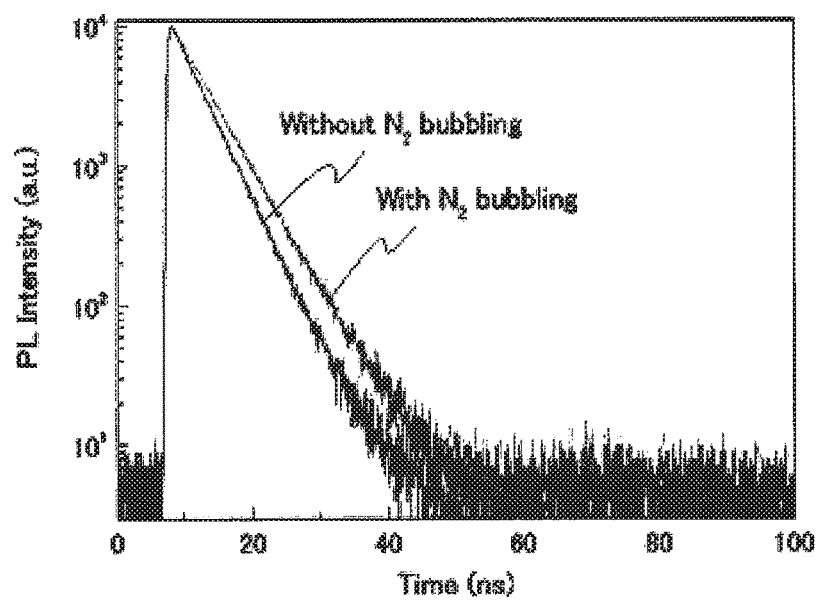
FIG. 13 is the transient decay curves of the toluene solution of the compound 21 in Example 6.

The production and the evaluation of the toluene solution were performed in the same manner as in Example 1 except that the compound 21 synthesized in Synthesis Example 6 was used at a concentration of $10^{-5}$ M instead of the compound 1. FIG. 12 shows the absorption-emission spectra at an excitation wavelength of 356 nm, and FIG. 13 shows the transient decay curves at an excitation wavelength of 340 nm. Light emission with a peak at 430 nm was observed. Fluorescent light having an excitation lifetime of 4.0 ns was observed in the toluene solution of the compound 21 before bubbling with nitrogen, and fluorescent light having an excitation lifetime of 4.9 ns was observed in the toluene solution of the compound 21 after bubbling with nitrogen. The photoluminescent quantum efficiency at an excitation wavelength of 320 nm of the compound was 15.1% before bubbling with nitrogen and 23.5% after bubbling with nitrogen.

Example 7

Production and Evaluation of Solution of Compound 22 (Solution)

Figure 14:
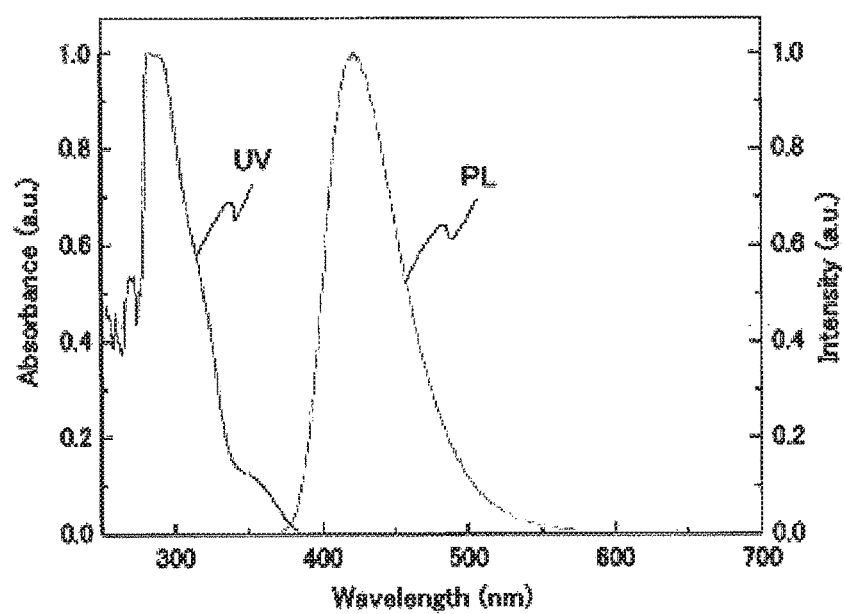
FIG. 14 is the absorption-emission spectra of the toluene solution of the compound 22 in Example 7.
Figure 15:
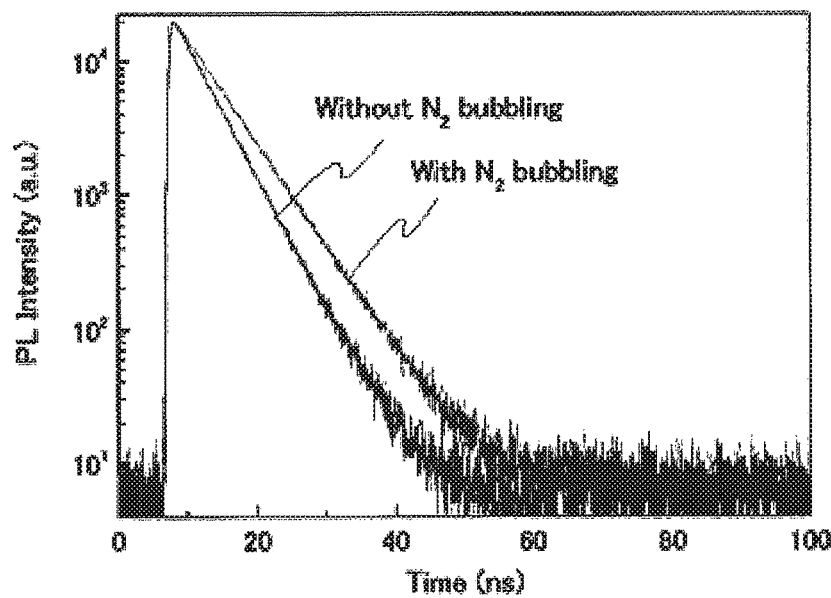
FIG. 15 is the transient decay curves of the toluene solution of the compound 22 in Example 7.

The production and the evaluation of the toluene solution were performed in the same manner as in Example 1 except that the compound 22 synthesized in Synthesis Example 7 was used at a concentration of $10^{-5}$ M instead of the compound 1. FIG. 14 shows the absorption-emission spectra at an excitation wavelength of 346 nm, and FIG. 15 shows the transient decay curves at an excitation wavelength of 340 nm. Light emission with a peak at 422 nm was observed. Fluorescent light having an excitation lifetime of 4.3 ns was observed in the toluene solution of the compound 22 before bubbling with nitrogen, and fluorescent light having an excitation lifetime of 5.5 ns was observed in the toluene solution of the compound 22 after bubbling with nitrogen. The photoluminescent quantum efficiency at an excitation wavelength of 320 nm of the compound was 21.7% before bubbling with nitrogen and 30.8% after bubbling with nitrogen.

Example 8

Production and Evaluation of Thin Film of Compound 1

Figure 16:
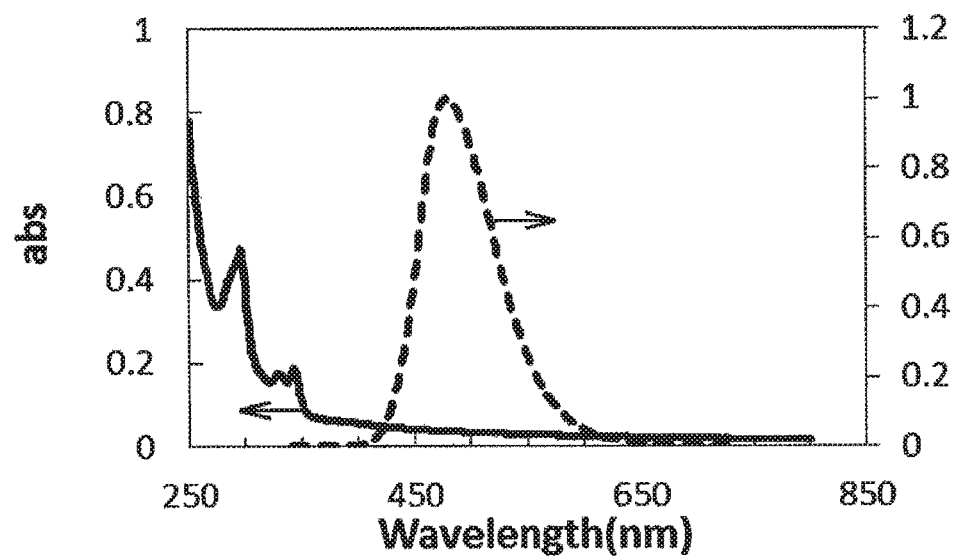
FIG. 16 is the absorption-emission spectra of the thin film in Example 8.

The compound 1 and mCP were vapor-deposited from separate vapor deposition sources on a quartz substrate by a vacuum vapor deposition method under a condition of a vacuum degree of $10^{-4}$ Pa or less to form a co-depositing thin film having a thickness of 100 nm having a concentration of the compound 1 of 6.0% by weight. FIG. 16 shows the absorption-emission spectra of the thin film. Light emission with a peak at 479 nm was observed.

Example 9

Production and Evaluation of Organic Electroluminescent Device Using Compound 1

Thin films were laminated on a glass substrate having formed thereon an anode formed of indium tin oxide (ITO) having a thickness of 100 nm, by a vacuum vapor deposition method at a vacuum degree of $5.0 \times 10^{-4}$ Pa. Firstly, HATCN was formed to a thickness of 10 nm on ITO, TrisPCz was formed to a thickness of 20 nm, and then mCP was formed to a thickness of 10 nm thereon. Subsequently, the compound 1 and mCP were co-deposited thereon from separate vapor deposition sources to form a layer having a thickness of 15 nm, which was designated as a light emitting layer. At this time, the concentration of the compound 1 was 6.0% by weight. PPT was then formed to a thickness of 10 nm, and BPyTp2 was formed to a thickness of 40 nm. Furthermore, lithium fluoride (LiF) was vacuum vapor-deposited to a thickness of 0.8 nm, and then aluminum (Al) was vapor-deposited to a thickness of 80 nm to form a cathode, thereby completing an organic electroluminescent device.

Figure 17:
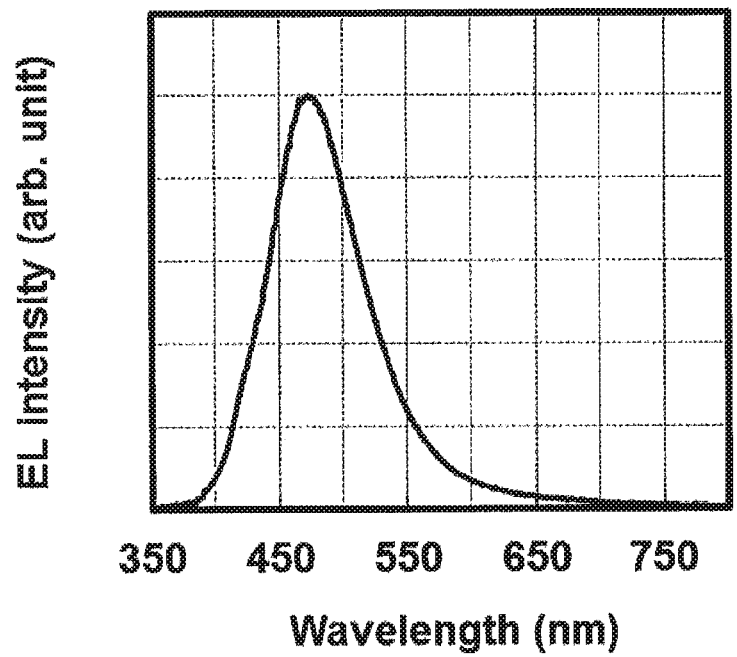
FIG. 17 is the light emission spectrum of the organic electroluminescent device in Example 9.
Figure 18:
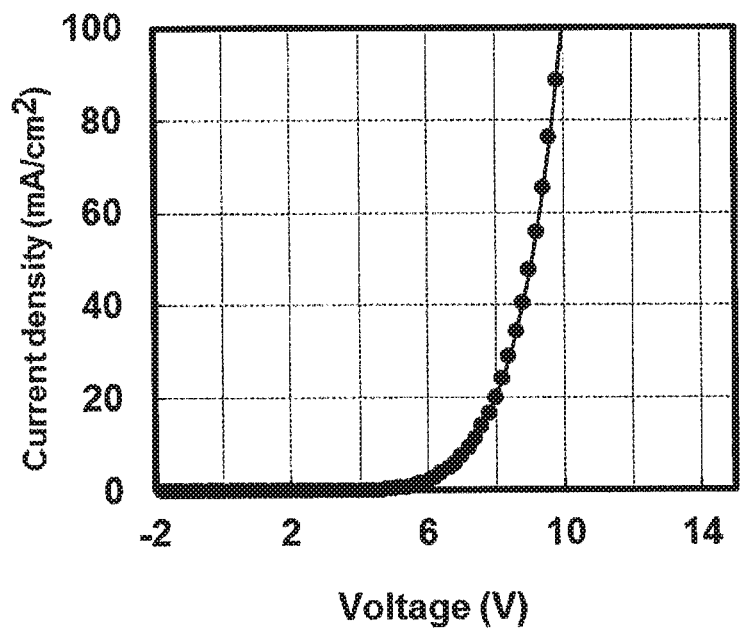
FIG. 18 is a graph showing the voltage-current density characteristics of the organic electroluminescent device in Example 9.
Figure 19:
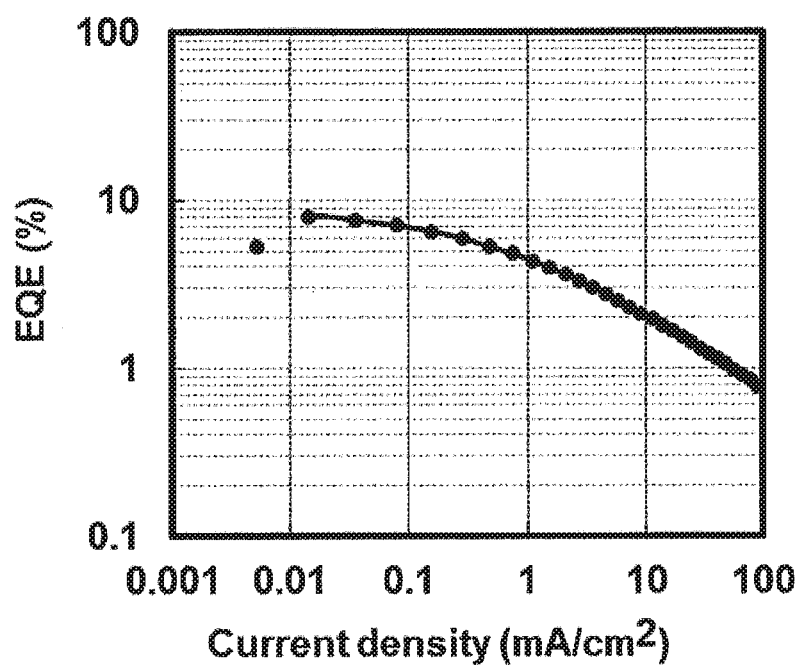
FIG. 19 is a graph showing the current density-external quantum efficiency characteristics of the organic electroluminescent device in Example 9.

FIG. 17 shows the light emission spectrum of the organic electroluminescent device thus produced, FIG. 18 shows the voltage-current density characteristics thereof, and FIG. 19 shows the current density-external quantum efficiency char-acteristics thereof. Light emission with a peak at 488 nm was observed, and a high external quantum efficiency of 7.9% was achieved.

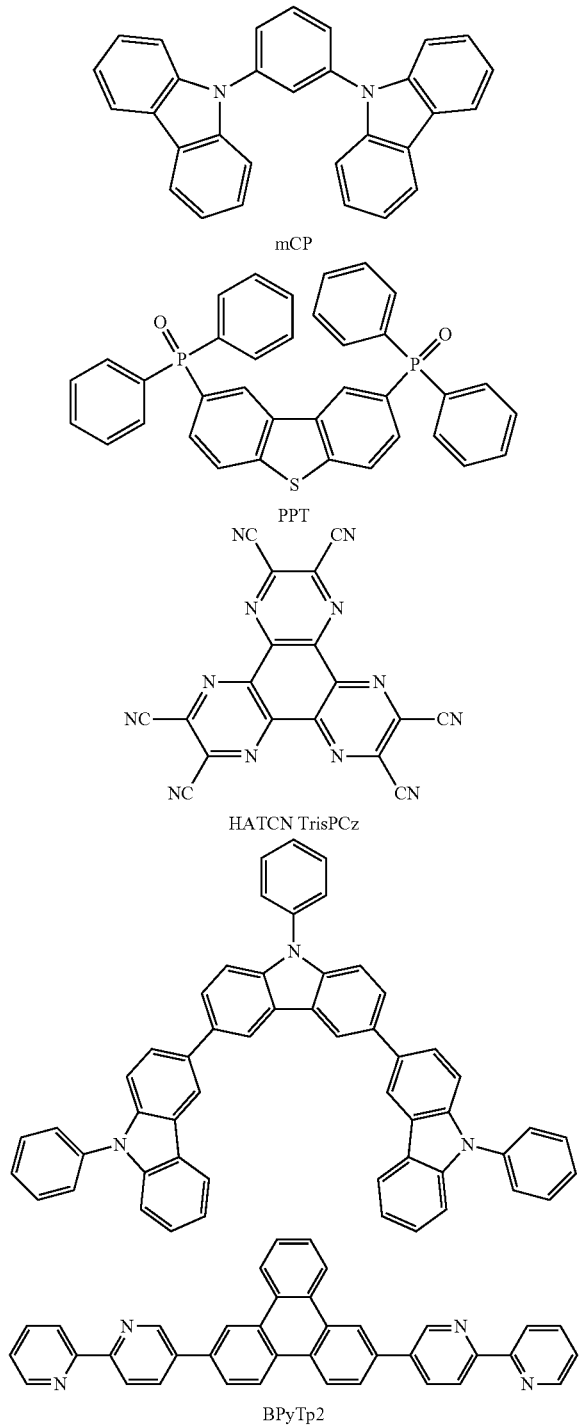

INDUSTRIAL APPLICABILITY

The compound of the invention is useful as a light emitting material. Accordingly, the compound of the invention may be effectively used as a light emitting material of an organic light emitting device, such as an organic electroluminescent device. The compound of the invention includes a compound that emits delayed fluorescent light, and thus may be capable of providing an organic light emitting device having a high light emission efficiency. Thus, the invention has high industrial applicability.

REFERENCE SIGNS LIST

1 substrate
2 anode
3 hole injection layer
4 hole transporting layer
5 light emitting layer
6 electron transporting layer
7 cathode

The invention claimed is:

1. An organic light emitting device comprising a substrate having thereon a light emitting layer containing a compound represented by the following general formula (1):

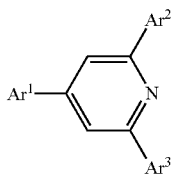

General Formula (1)

wherein in the general formula (1), $Ar^1$ represents an unsubstituted aryl group, $Ar^2$ and $Ar^3$ are the same as each other and represent an aryl group substituted with a group represented by the following general formula (2):

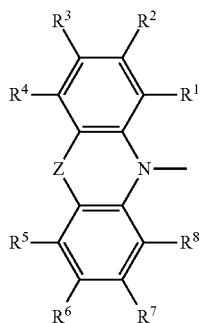

General Formula (2)

wherein in the general formula (2), $R^1$ to $R^8$ each independently represent a hydrogen atom or a substituent; Z represents O, S, or $R^9$—N; and $R^9$ represents a hydrogen atom or a substituent, provided that $R^1$ and $R^2$, $R^2$ and $R^3$, $R^3$ and $R^4$, $R^5$ and $R^6$, $R^6$ and $R^7$, and $R^7$ and $R^8$ each may be bonded to each other to form a cyclic structure, provided that the compound emits light.

2. The organic light emitting device according to claim 1, wherein the organic light emitting device emits delayed fluorescent light.

3. The organic light emitting device according to claim 1, wherein the organic light emitting device is an organic electroluminescent device.

4. The organic light emitting device according to claim 1, wherein the compound is contained in the light emitting layer in an amount of 10% by weight or less.

5. The organic light emitting device according to claim 1, wherein the light emitting layer consists of the compound.

6. The organic light emitting device according to claim 1, wherein the light emitting layer contains the compound and a host material.

* * * * *